(12) United States Patent
Schaff et al.

(10) Patent No.: US 6,708,141 B1
(45) Date of Patent: *Mar. 16, 2004

(54) METHOD FOR MODELING CELLULAR STRUCTURE AND FUNCTION

(75) Inventors: James C. Schaff, Cheshire, CT (US); John Carson, West Hartford, CT (US); Leslie Loew, West Hartford, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/407,383

(22) Filed: Sep. 28, 1999

Related U.S. Application Data

(63) Continuation-in-part of application No. 09/008,649, filed on Jan. 16, 1998, now Pat. No. 6,219,440.
(60) Provisional application No. 60/102,071, filed on Sep. 28, 1998.

(51) Int. Cl.[7] .................. G06G 7/60; G06N 7/00; G06F 7/64
(52) U.S. Cl. .................. 703/2; 703/11; 702/19
(58) Field of Search .................. 702/19; 382/128; 703/2, 11

(56) References Cited

U.S. PATENT DOCUMENTS

| | | | |
|---|---|---|---|
| 4,841,479 A | * 6/1989 | Tsuji et al. | 364/900 |
| 5,025,388 A | 6/1991 | Cramer, III et al. | 364/496 |
| 5,029,119 A | 7/1991 | Konno | 716/20 |
| 5,307,287 A | 4/1994 | Cramer, III et al. | 364/496 |
| 5,424,963 A | 6/1995 | Turner et al. | 703/6 |
| 5,446,652 A | 8/1995 | Peterson et al. | 703/6 |
| 5,446,860 A | 8/1995 | Dresser et al. | 711/100 |
| 5,446,870 A | 8/1995 | Hinsberg, III et al. | 703/6 |
| 5,826,065 A | 10/1998 | Hinsberg, III et al. | 717/1 |
| 5,914,891 A | 6/1999 | McAdams et al. | 703/11 |
| 6,219,440 B1 | * 4/2001 | Schaff et al. | 382/128 |

OTHER PUBLICATIONS

Cash, D.J., et al., (Nov. 1988) Biophysical Journal, vol. 54, No. 5, pp. 909–919.*
Jones, D.T., et al., (1994) Biochemistry, vol. 33, No. 10, pp. 3038–3049.*
Kafahl, R.H., et al., (1984) Adv. Exp. Med. Biol., vol. 169, pp. 103–123.*
Quon, M.J., et al., (1991) J of Theoretical Biology, vol. 150, No. 1, pp. 59–72.*

* cited by examiner

*Primary Examiner*—John S. Brusca
*Assistant Examiner*—Marjorie A. Moran
(74) *Attorney, Agent, or Firm*—Cantor Colburn LLP

(57) ABSTRACT

A method and apparatus for modeling cellular structure is disclosed. The system incorporates a theoretical hypotheses of cellular physiology into a simulation framework that allows direct comparison of simulation results with experimental data. The description of the biological model is kept independent of the solution by the use of an integrated anatomical and physiological modeling language. This framework allows complex heterogeneous intracellular chemical simulations to be built with little or no knowledge of the underlying numerical methods. Because the simulation results are easily compared to the experimental results, the user can more easily confirm the hypothesis.

19 Claims, 24 Drawing Sheets

Experimental Images

Mouse Neuroblastoma loaded with Indo 1

Applied Bradykinin at t=0 t = 6 seconds t = 7 seconds t = 8 seconds t = 9 seconds t = 10 seconds

METHOD FOR MODELING CELLULAR STRUCTURE AND FUNCTION

CROSS REFERENCE TO RELATED APPLICATIONS

This application is a continuation-in-part of U.S. patent application Ser. No. 09/008,649 filed Jan. 16, 1998, now U.S. Pat. No. 6,219,440 the entire contents of which are incorporated herein by reference, and this application claims the benefit of U.S. provisional patent application Ser. No. 60/102,071 filed Sep. 28, 1998, the entire contents of which are incorporated herein by reference.

BACKGROUND OF THE INVENTION

The invention relates in general to cell simulation and in particular to a method and apparatus for modeling cellular structure and function which produces simulation data that is easily comparable to experimental data.

Tools such as fluorescent probes and confocal microscopy have enabled the resolution of three dimensional intracellular spatial distribution of different molecular species as well as sub-cellular structures. Research in cellular physiology requires the formation of theoretical hypotheses regarding the experimentally observed phenomena. These hypotheses are often formalized into mathematical models, and then tested by incorporating these models into simulations.

The deficiencies in existing technology originates from the current limitations of the cellular representation. Cells are represented as ideal and simple geometric shapes consisting of spatially homogeneous behavior (physiology) and structure (anatomy). This prevents the researcher from expressing an observed physiological phenomena in a simulation that maps easily to an actual experiment of an intact cell. Thus the validation of the model, and hence the hypothesis, is made very difficult.

Most current efforts in the modeling and simulation of cellular physiology are directed toward either very specific models of individual mechanisms or abstract representations of more complex phenomena. The specific models include models of individual molecular interactions such as ion channels gathered from biochemistry and electrophysiology research. The abstract models apply simplifications of the underlying mechanisms that are usually only appropriate to explain a small class of physiological problems.

Some typical abstractions include simplified simulation geometry, such as cable theory applied to nerve action potentials (where elementary features are uniform cross sections of nerve processes), or spatially homogenous grids with cell boundaries defined by geometric primitives (planes, spheres, cylinders). Additional abstractions include representing complex physiology in terms of a small number of variables with terms that try to approximate the overall effect of the underlying physiology (simple models of cellular signaling such as calcium dynamics).

Efforts to address the complexity of physiology also tend to concentrate on intercellular phenomena. The cellular automata approach looks at intercellular interactions where the fundamental computational unit represents an entire cell. There has also been numerous simulations in neurophysiology involving models based on cable theory. These models decompose a single neuronal cell into computational elements representing entire cross sections of axons and dendrites. While these models reproduce the external behavior of action potentials in neurons with good fidelity, the inherent geometric simplicity of the formulation restrict their application to the class of problems where the cell interior can be considered a completely homogenous conductive media.

Interest has been shown in the collection of current physiological knowledge in a computer usable form. An example of this is SENEX, a computer based representation of cellular signal transduction processes in the central nervous system. This is an object oriented classification structure of biologic entities and significant relationships among them. However, their representation of biological entities and relationships are not in the form of actual mathematical models, and thus can not be used directly for simulations.

Present technology lacks good spatial correlation from simulation to empirical data. Typical simulations utilize an idealized geometry such as a cylinder, sphere, or plane rather than representing the geometry of an actual cell. The simulations are also spatially homogeneous, thus every part of the simulation has the same basic behavior, in contrast with actual cells. Thus, comparison of simulation with experiment is difficult or impossible.

SUMMARY OF THE INVENTION

The above-discussed and other drawbacks and deficiencies of the prior art are overcome or alleviated by the method and apparatus for modeling cellular structure and function of the present invention. The present invention incorporates a theoretical hypotheses of cellular physiology into a simulation framework that allows direct comparison of simulation results with experimental data. The description of the biological model is kept independent of the solution by the use of an integrated anatomical and physiological modeling language. This framework allows complex heterogeneous intracellular chemical simulations to be built with little or no knowledge of the underlying numerical methods. Because the simulation results are easily compared to the experimental results, the user can more easily confirm the hypothesis.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DETAILED DESCRIPTION OF THE INVENTION

Figure 1:
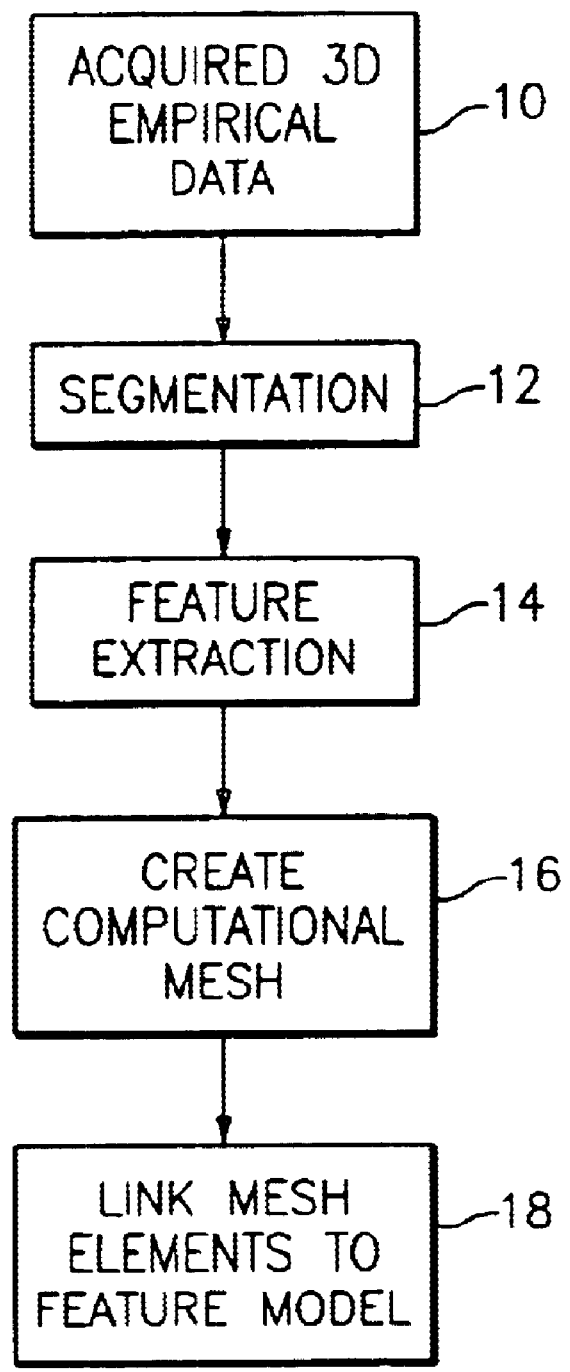
FIG. 1 is a flowchart of the method for creating the simulation volume.
Figure 2:
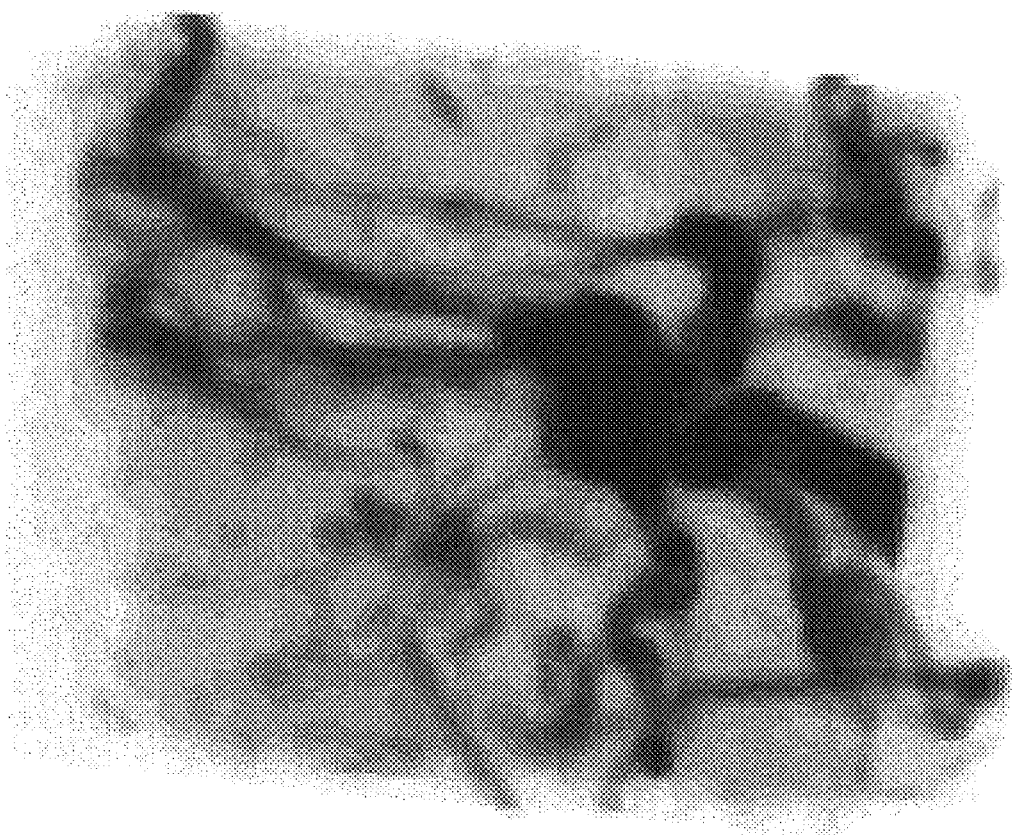
FIG. 2 is an illustration of a three dimensional image from a confocal microscope.
Figure 3:
FIG. 3 is an illustration of the image of FIG. 2 segmented.
Figure 4:
FIG. 4 is an illustration of a three dimensional volume of simulation elements derived from the segmented image in FIG. 3.
Figure 5:
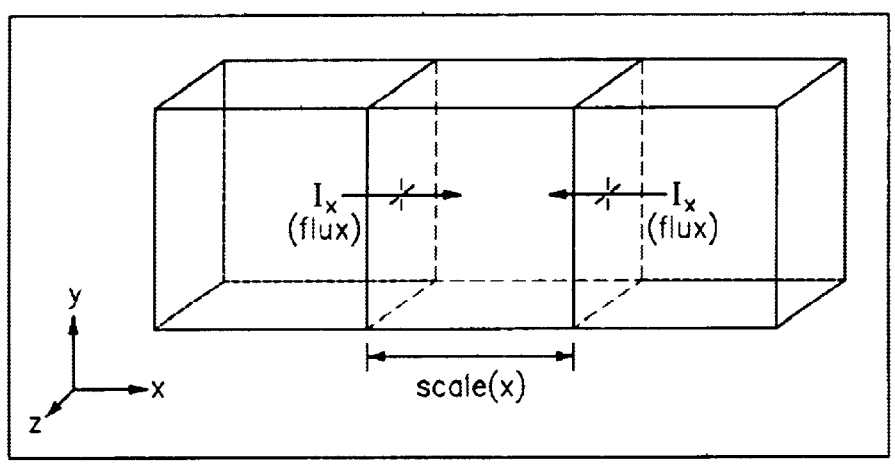
FIG. 5 is an illustration of three simulation elements using an orthogonal finite volume approach.

The invention is directed to simulation of cellular physiological and anatomical parameters. The invention first creates a simulation domain based on an n-dimensional geometric or spatial description of the cell. An exemplary n-dimensional geometric description is a three dimensional image. A simulation volume is created and then simulation is performed by modeling the behavior, physiological and/or anatomical, of simulation elements making up the simulation volume. FIG. 1 is a flowchart of the routine performed to create the simulation volume. At step 10, three dimensional empirical data of the cell is acquired using known techniques (e.g. confocal microscopy). FIG. 2 is an exemplary three dimensional image from a confocal microscope. It is understood that the an n-dimensional geometric or spatial description may be other than an image from a confocal microscope. The cell is isolated through a three dimensional segmentation step 12 and the cellular physiology is determined at feature extraction step 14. FIG. 3 is a three dimensional image showing the result of the segmentation operation. At step 16, the three dimensional empirical data is used to generate a simulation volume made up of a plurality of simulation elements or other computational meshes. FIG. 4 is a diagram of the three dimensional simulation volume created from the segmented image of FIG. 3. Three simulation elements are shown in FIG. 5. The simulation volume is created by sampling the three dimensional empirical data to form a plurality of simulation elements. Each simulation element represents the physiology of a single class of cellular features determined in the feature extraction step 14. Lastly, at step 18 each simulation element is then linked to a stored model corresponding to the physiology of the simulation element. It is understood that regions of the biological material may be linked to models prior to imposing the computational mesh on the n-dimensional description of the biological material. Thus, the order of steps in FIG. 1 is exemplary. The models used are described in more detail below. In this way, the simulation volume is made up of a plurality of simulation elements, each being associated with a model describing its behavior. In an alternative embodiment described herein, features of the cell, derived at feature extraction step 14, are linked to models and modeled as regions instead of as individual simulation elements.

The utilization of n-dimensional geometric description (such as a 2D or 3D image) is helpful in executing the simulation model. The anatomical features of the cell are identified and extracted as geometric descriptions. These geometric descriptions are sampled to create a simulation volume. This simulation volume represents a spatially heterogeneous collection of three dimensional simulation elements as shown in FIGS. 4 and 5, where each simulation element corresponds to each identified anatomical feature in position and function. Comparison of simulation results and observed behavior is facilitated because the microscopy data and the simulation model are mapped onto the same geometry. Geometric models, simulation elements, and original 3D images can all be rendered into the same 3D scene. They are all mapped to the same coordinate system for ease of viewing and comparison. In addition, both the simulation elements and the empirical data can be formatted as series of images that can be viewed easily. Simulation results can be directly correlated with experimental time series volume datasets. Thus, the model can be modified until the experimental results are duplicated. The same physiological models can be verified in multiple experiments (different geometry and different stimuli). The present invention provides a framework for encapsulating knowledge about the interaction of intracellular components.

In accordance with another aspect of the invention, by generating a simulation volume in which each element corresponds to a single class of physiological features, simulation of the entire cell is simplified. Current simulation efforts establish a model as a a single set of ordinary and partial differential equations that represents all cellular physiology of interest. This requires more complex mathematical descriptions and the resulting interactions between simulation elements are not as easily separable in terms of their physiological origins. An embodiment of the present invention establishes the simulation as a spatially heterogeneous collection of simulation elements as shown in FIG. 5, where each element represents only the physiology of a single class of cellular features. This allows complex behavior to be simulated using a collection of simple models. Each simple model maps directly to a biological feature and encapsulates only the physiology associated with that feature. In an alternative embodiment described herein, the entire region or feature (e.g., ER) is linked to a model for that feature and simulated instead of using individual simulation elements. The model describes how it varies the concentration of each molecular species within the bounds of an element and how it interacts with its immediate environment. Thus, an assembly of different elements can interact with complex behavior even though their individual behavior may be simple. This organization more closely approximates the actual dynamics within the cell and allows the modeling of each feature to be independent, and therefore simpler.

Yet another aspect of the invention is the use of abstract physiological models in developing classes of biological entities. An example is a feature model which encapsulates the physiological behavior corresponding to a single area or compartment (endoplasmic reticulum, nucleus, cytosol, extracellular, etc.) within a particular cell type. The process of creating a library of accepted feature models can be a powerful tool for encapsulating knowledge of general physiological function.

Each feature consists of a collection of reaction models and molecular species models and the behavior of the resulting feature model is the result of these coupled reactions. These reactive models are categorized as volume reactions (i.e. reactions within an element) and membrane reactions (e.g. pumps and channels including binding and trans-membrane fluxes). As an example, an IP3 receptor (membrane reaction model) may be specified as part of an endoplasmic reticulum feature.

The modeling framework defines a variety of components including the reaction models to be used, initial conditions and other parameters described herein. The user defines the modeling framework using either a cellular simulation description language or a graphical user interface.

In an exemplary embodiment of the invention, a cellular simulation description language has been implemented where the geometry is based on a subset of Silicon Graphic's Inventor® 3D Scene Description Language, extended to deal with constructive solid geometry and volume datasets. This language was then further extended to introduce biological descriptions and a simulation definition. A graphical abstraction of these files has been generated to allow more natural interaction with the models and simulation results. This interactive graphical user interface provides some model analysis tools as well as simulation control.

Yet another aspect of the invention is the use of a model geometry that corresponds with the geometry of the empirical volumetric data. The spatial organization of cellular structure is represented by a collection of feature models that correspond to identified cellular features. These cellular features can be identified by three dimensional segmentation and feature extraction from an n-dimensional representation (e.g., image). The feature extraction is simplified if cellular structures are labeled using fluorescent probes that are specific to that structure.

For cellular structure that is either too small (e.g. mitochondria) or too convoluted (e.g. endoplasmic reticulum) to be extracted easily from actual data, feature geometry may be approximated by synthetic geometry. This synthetic geometry can consist of any combination of geometric primitives (e.g. sphere, cylinder), mathematically defined solid models (e.g. fractal solids), or arbitrary polygonal surfaces (e.g. CAD models). Alternatively, features that are too small for appropriate representation may be assumed to be evenly distributed within the cell compartment (e.g. ER may be continuously distributed within cytosol) while maintaining separate models for the compartment feature and the evenly distributed feature. Once features are extracted, they are classified by their underlying physiology, and are linked to the appropriate feature models for use in simulation.

The invention may simulate chemical dynamics, mechanical dynamics or a combination of chemical and mechanical dynamics. The model of species interaction for simulating chemical dynamics includes diffusion in the presence of an electric field, chemical reactions, and membrane transactions due to pumps and channels. Prior to describing the chemical dynamics model in detail, concepts underlying the diffusion in the presence of an electric field will be described.

The model consists of a set of continuous equations relating the state variables of the system and the input (stimuli). The set of state variables consists of the concentrations of each molecular species $C_i$ and the electric potential V defined over a subset of three dimensional space for time greater than zero. State variables are defined such that knowledge of their values at time t=T is sufficient to determine the behavior of the whole model at any time t>T for any known stimulus. In general, the model itself can be a function of position (heterogeneous) and also of the state variables (nonlinear).

The model uses electrodiffusion/reaction equations to determine molecular flux. According to the Nernst-Plank Equation, the molecular flux $\vec{J}_i$ due to diffusion and electric forces is as described in equation (1). Note that the subscript i denotes values pertaining to the $i^{th}$ molecular species.

$$1) \quad \vec{J}_i = -D_i \nabla C_i - z_i \mu_i C_i \nabla V, \text{ where } \mu_i = \frac{D_i F}{RT}$$

Where $C_i$ is the concentration, $D_i$ is the diffusion constant, $z_i$ is the ionic valence, $m_i$ is the mobility, V is the electric potential, F is Faraday's constant, R is the gas constant, and T is the absolute temperature. The first term of (1) describes the diffusion flux, the second term of (1) describes the flux due to the electric field.

The time rate of change of species concentration defined over an infinitesimally small volume is the sum of the net flux into the volume and the net reaction rate $$2) \quad \frac{\partial C_i}{\partial t} = -\nabla \cdot (\vec{J}_i) + S_i(C_1, C_2, \ldots C_N)$$

where $S_i$ defines the net chemical reaction rate for species $C_i$.

The model also uses electrical potential equations to define electric flux density. The electric potential can be defined everywhere according to the laws of electrostatics. Gauss's law (3) states that the net charge Q within a closed surface is equal to the net electric flux density $\vec{D}$ leaving that surface.

$$3) \quad Q = \oint_S \vec{D} \cdot d\vec{S}$$

and $\vec{D}$ is related to the permittivity (or dielectric constant) e, the electric field $\vec{E}$ and electric potential V according to $$4) \quad \vec{D} = \epsilon \vec{E} = -\epsilon \nabla V$$

The total charge within a volume can be defined as the concentration of molecular species $C_i$, the ionic valence $z_i$, and Faraday's constant F integrated over that volume.

$$5) \quad Q = \oint_V \left[ \sum_i z_i F C_i \right] dv$$

Combining (3), (4) and (5) gives a form of Gauss's Law (6) that can be evaluated for an incremental volume and relates electric potential to ionic concentrations.

$$6) \quad \oint_v \left[ \sum_i z_i F C_i \right] dv = \oint_S (-\epsilon \nabla V) \cdot d\vec{S}$$

The electric potential can also be defined as a function of electric currents through a conductive media and across capacitive boundaries. Conservation of charge states that in a conductor, the net current density $\vec{J}$ leaving any closed surface $d\vec{S}$ is equal to 0. This formulation assumes that the interior of all connected regions within a cell simulation (cytosol, ER lumen, extracellular milieu, etc.) can be modeled as conductors. This implies that the relaxation time of a free charge placed in the interior (lumen) to the surface (membrane) is much faster than the cellular dynamics of interest.

$$7) \quad -\frac{dQ}{dt} = \oint_S \vec{J} \cdot d\vec{S} = 0$$

$\vec{J}$ is related to the conductance 1, and the electric potential V according to Ohm's Law (8)

8) $\vec{J} = -\lambda \nabla V$ where $\lambda = \sum_i z_i \mu_i C_i$ for the interior of a conductor (Cell or organelle body), and for the current density normal to a membrane $J_n$ is related to the membrane specific capacitance Cm, and the net charge flux density passing through the membrane Jm (via pumps, channels, etc.) according to 9) $J_n = -C_m \dfrac{\partial (V - V_{opposite})}{\partial t} + J_m$ substituting (8) and (9) into (7) gives a form of conservation of current that can be applied to both membranes and interior spaces with less geometric constraints than standard cable theory.

The specific chemical dynamics simulation will now be described. The specification of the chemical dynamics simulation is very flexible. The simulation description specifies the molecular species to be simulated, parameters to be logged, the number of elements in each dimension, the size of the elements, and the simulation time step. A chemical dynamics simulation is created by sampling all or part of the model geometry into a three dimensional mesh of simulation elements. FIG. 5 shows three elements of a uniform orthogonal mesh. The chemical dynamics are modeled at the concentration level where dynamics is described as fluxes of molecular species across boundaries separating adjacent elements and chemical reactions within the same element as shown FIG. 6. These fluxes can be functions of diffusion, ion drift, membrane potential, membrane transport (including pumps and channels) or any other relationship involving the spatial distribution of molecular species. Membranes may be represented by element boundaries separating dissimilar elements. The state variables consist of the concentration distribution of every molecular species as well as membrane potential.

The chemical dynamics are described as reactions with elements and fluxes of molecular species across boundaries separating adjacent elements. These fluxes can be functions of diffusion, ion drift, membrane potential, chemical reaction, or any other relationship involving the spatial distribution of molecular species. Membranes are represented by element boundaries separating dissimilar elements. The collection of all concentrations of each molecular species within each simulation element and the electric potential in each simulation element constitutes the state variables of the system.

The number of species defined in a simulation will affect the complexity of the model used for the simulation. Each additional species introduces complexity in two ways.

(1) One or more chemical reactions in the model may become active in the simulation if the additional species complete the minimum set of reagents/products.

(2) Active reaction models may assume a more complicated form that incorporates the effects of the additional species.

Both local and membrane reactions are constructed of a hierarchical assembly of models (rate equations) of differing complexity. The model selected for a given reaction is the simplest form that incorporates all of the relevant reagents currently defined by a simulation.

The numerical solution to all of the model equations is achieved by a conventional finite volume method. This method is based on the sub-domain formulation of the method of weighted residuals, although the resulting discrete equations resemble those of the finite-difference method. The finite volume method allows for very good control of boundary conditions and profile assumptions while preserving the conservative nature of many of the equations of interest. Examples of models exhibiting conservative behavior is Fick's Law and Gauss's Law, which mandates conservation of mass flux and electric flux density respectively.

The fundamental step in the numerical solution of a set of equations involves integrating them in time and over space over a single volume element using appropriate interpolation profiles and boundary conditions. The solution of each integration relates a small neighborhood of sample values over space and time. As shown in FIG. 5, boundary conditions for individual elements in the chemical simulation framework guarantee mass conservation. The flux is calculated by the Nernst-Plank equation when the neighboring elements are of similar type. The flux is based on membrane reactions (channels, pumps . . . ) when the neighboring elements are different.

The resulting equations are solved by an implicit method using an iterative solution by the line by line method. This is an implicit method that guarantees stability when the models used in the simulation obeys some simple and physically appropriate constraints. The ability of each iteration to converge to the solution of the non-linear equations is made possible by adaptive underrelaxation scheme. The simulation geometry is assumed to be uniformly sampled orthogonal elements (cubes). Unless otherwise noted, piecewise linear interpolation (basis) functions are used to interpret the values of molecular concentrations and electric potentials between element centers.

Within uniformly sampled orthogonal elements, the first term on the right side of equation (2) can be expressed as the sum of the fluxes entering the volume element from its six adjacent neighbors. This flux is composed of electrodiffusion and membrane transport. Here J is defined as the net molecular flux across any surface of the volume element, and is assumed to be constant over that element boundary.

10) $-\nabla \cdot (\vec{J}_i) = \text{Area}_{boundary} \cdot [Jx|_{x+} - Jx|_{x-} + Jy|_{y+} - Jy|_{y-} Jz|_{z+} - Jz|_{z-}]$ The x, y and z components of the molecular flux Jx, Jy, and Jz are evaluated at the 6 element boundaries by assuming them to be constant across each boundary surface. The molecular fluxes depends on the element boundary conditions as follows (see Table 1). The simulation boundary conditions of either fixed concentration, or of fixed molecular flux are easily applied.

TABLE 1

Discrete formulation for molecular flux

| Boundary Condition | Expression for molecular flux |
|---|---|
| Similar Elements | $J_x\|_{x+} = -D_i \nabla C\|_{x+} - z_i \mu_i C_i \nabla V\|_{x+}$ <br> $= D_i \dfrac{C_i(x) - C_i(x+1)}{\Delta x} +$ <br> $z_i \mu_i \cdot C_i\|_{x+} \cdot \dfrac{V(x) - V(x+1)}{\Delta x}$ |
| Dissimilar Elements (membrane) | $J_x\|_{x+} =$ flux due to membrane transport <br> $= f(C_1, C_2, \ldots C_N, V)$ |

TABLE 1-continued

Discrete formulation for molecular flux

| Boundary Condition | Expression for molecular flux |
|---|---|
| Simulation Boundary (specified conc.) | $J_x\|_{x+} = -D\nabla C\|_{x+} = D\dfrac{C(x) - C_{boundary}}{\Delta x/2}$ |
| Simulation Boundary (specified flux) | $J_x\|_{x+} = J_{boundary}$ |

The numerical approach is described by considering a simplified equation in terms of molecular flux J and source term S.

11) $\dfrac{\partial C}{\partial t} = -\nabla \cdot \vec{J} + S$ next, this equation is integrated over the time interval and over the volume of an element.

12) $\int_{t}^{t+\Delta t}\int_{x-}^{x+}\int_{y-}^{y+}\int_{z-}^{z+} \dfrac{\partial C}{\partial t} dz\,dy\,dx\,dt = \Delta x \Delta y \Delta z (C_P - C_P^{old})$ 13) $\int_{t}^{t+\Delta t}\int_V (-\nabla \cdot \vec{J} + S) dv\,dt = \Delta t\{\Delta y \Delta z (J_{x-} - J_{x+}) +$
$\Delta x \Delta z (J_{y-} - J_{y+}) +$
$\Delta x \Delta y (J_{z-} - J_{z+}) + \Delta x \Delta y \Delta z S\}$ so, 14) $\dfrac{vol}{\Delta t}(C_P - C_P^{old}) = \text{area} \cdot (J_{x-} - J_{x+} + J_{y-} -$
$J_{y+} + J_{z-} - J_{z+}) + \text{vol} \cdot \text{Source}$ for internal elements, a molecular flux defined at x+ ($J_{x+}$) is defined as follows:

15)

$J_x\|_{x+} = -D_i \nabla C\|_{x+} - z_i \mu_i C_i \nabla V\|_{x+}$ $\left(\left(\left(= D_i C_i(x) - \dfrac{C_i(x+1)}{\Delta x} + z_i \mu_i \cdot C_i\right|\right)\right)_{x+} \cdot \dfrac{V(x) - V(x+1)}{\Delta x}$ 16) $\dfrac{h^3}{\Delta t}(C_P - C_P^{old}) = D \cdot h(C_E - C_P) + \mu \cdot h \cdot \dfrac{C_E + C_P}{2} \cdot$
$(V_E - V_P) + D \cdot h(C_W - C_P) + \mu \cdot h \cdot$
$\dfrac{C_W + C_P}{2} \cdot (V_W - V_P) + D \cdot h(C_N - C_P) +$
$\mu \cdot h \cdot \dfrac{C_N + C_P}{2} \cdot (V_N - V_P) +$
$D \cdot h(C_S - C_P) + \mu \cdot h \cdot \dfrac{C_S + C_P}{2} \cdot (V_S - V_P) +$
$D \cdot h(C_F - C_P) + \mu \cdot h \cdot \dfrac{C_F + C_P}{2} \cdot$
$(V_F - V_P) + D \cdot h(C_B - C_P) + \mu \cdot h \cdot$
$\dfrac{C_B + C_P}{2} \cdot (V_B - V_P) + h^3 \cdot \text{Source}$ The terms of C are collected to form the matrix coefficients (Equ: 17)

$A_P C_P + A_E C_E + A_W C_W + A_N C_N + A_S C_S + A_F C_F + A_B C_B = B + A_{P0} C_P^{old}$ where:

$A_P = A_{P0} - h^3 \cdot S_{proportional} + \sum_\alpha A_\alpha$ $A_{P0} = \dfrac{h^3}{\Delta t}$ 18) $A_\alpha = \begin{cases} D \cdot h & \text{no membrane at } \alpha \\ D_{membrane} \cdot h & \text{membrane at } \alpha \end{cases}$ $B = h^3 \cdot S_{constant} + h^2 \cdot \sum_\alpha Jm_\alpha + h \cdot \sum_\alpha B_\alpha$ $B_\alpha = \begin{cases} \mu z \dfrac{C_P + C_\alpha}{2}(V_\alpha - V_P) & \text{no membrane at } \alpha \\ \mu_{membrane} \cdot z \dfrac{C_P + C_\alpha}{2}(V_\alpha - V_P) & \text{membrane at } \alpha \end{cases}$ $\alpha = E, W, N, S, F, B$ Where chemical reactions are represented as a first order linearization $S_{constant}$, $S_{proportional}$ where Sp is constrained to be negative for stability reasons. Membrane reactions (in the context of species in solution) is represented by reactions with binding sites on the surface of the membrane, and as fluxes through the membrane. The binding site reactions are treated as in the above case (Sc and Sp). The fluxes are currently represented as some combination of a passive membrane term (defining an effective diffusion and mobility constant) and an arbitrary membrane flux term (Jm) to handle any non-linear terms.

Within an element, the left side of (6) becomes the sum of the average charges due to each molecular species. Assuming a linear profile of concentration between adjacent elements, the average concentration $\overline{C}_i$ over an element is computed as a linear combination of the sample concentration of the current element and it's nearest neighbors.

19) $\oint_v \left[\sum_i z_i F C_i\right] dv = \text{Volume} \cdot \sum_i z_i F \overline{C}_i$ 20) $\oint_S \vec{D} \cdot d\vec{S} = \text{Area} \cdot \{D_x\|_{x+} - D_x\|_{x-} + D_y\|_{y+} - D_y\|_{y-} + D_z\|_{z+} - D_z\|_{z-}\}$ Area and Volume refer to the size of a single element.

The x, y and z components of the electric flux density Dx, Dy, and Dz are evaluated at the 6 element boundaries by assuming them to be constant across each boundary surface. The electric potential of neighboring elements are then related by one of the forms of Table 2. The simulation boundary conditions of either fixed potential, or of fixed electric field (or electric flux density) are easily applied.

TABLE 2

Discrete formulation for electric flux density

| Boundary Condition | Expression for electric flux density, D |
|---|---|
| Similar Elements | $D_x\|_{x+} = -\nabla V\|_{x+} \varepsilon = \dfrac{V(x) - V(x+1)}{\Delta x}\varepsilon$ |
| Dissimilar Elements (capacitive membrane) | $D_x\|_{x+} = -\nabla V\|_{x+} \varepsilon = \dfrac{V(x) - V(x+1)}{\text{membrane} \Delta x}\varepsilon_{membrane}$ |

TABLE 2-continued

Discrete formulation for electric flux density

| Boundary Condition | Expression for electric flux density, D |
|---|---|
| Simulation Boundary (specified voltage) | $D_x\|_{x+} = -\nabla V\|_{x+}\varepsilon_{x+} = \dfrac{V(x) - V_{boundary}}{\Delta x/2}\varepsilon$ |
| Simulation Boundary (specified field) | $D_x\|_{x+} = \varepsilon_{x+}E_x = \varepsilon E_x$ |

The numerical approach is described by considering a simplified equation in terms of molecular flux J and source term S.

21) $\dfrac{\partial C}{\partial t} = -\nabla \cdot \vec{J} + S$ next, this equation is integrated over the time interval and over the volume of an element.

22) $\int_t^{t+\Delta t}\int_{x-}^{x+}\int_{y-}^{y+}\int_{z-}^{z+}\dfrac{\partial C}{\partial t}dz\,dy\,dx\,dt = \Delta x\Delta y\Delta z(C_p - C_p^{old})$ 23) $\int_t^{t+\Delta t}\int_V (-\nabla \cdot \vec{J} + S)dv\,dt = \Delta t\{\Delta y\Delta z(J_{x-} - J_{x+}) +$ $\Delta x\Delta z(J_{y-} - J_{y+}) +$ $\Delta x\Delta y(J_{z-} - J_{z+}) +$ $\Delta x\Delta y\Delta z S\}$ so, 24) $\dfrac{vol}{\Delta t}(C_p - C_p^{old}) = area \cdot (J_{x-} - J_{x+} + J_{y-} -$ $J_{y+} + J_{z-} - J_{z+}) +$ $vol \cdot Source$ for internal elements, a molecular flux defined at x+ ($J_{x+}$) is defined as follows:

25) $J_x\|_{x+} = -D_i\nabla C\|_{x+} - z_i\mu_i C_i\nabla V\|_{x+}$ $= D_iC_i(x) - \dfrac{C_i(x+1)}{\Delta x} + z_i\mu_i \cdot C_i\Big|_{x+}\cdot\dfrac{V(x) - V(x+1)}{\Delta x}$ 26) $\dfrac{h^3}{\Delta t}(C_P - C_P^{old}) = D\cdot h(C_E - C_P) + \mu\cdot h\cdot\dfrac{C_E + C_P}{2}\cdot$ $(V_E - V_P) + D\cdot h(C_W - C_P) + \mu\cdot h\cdot$ $\dfrac{C_W + C_P}{2}\cdot(V_W - V_P) + D\cdot h(C_N - C_P) +$ $\mu\cdot h\cdot\dfrac{C_N + C_P}{2}\cdot(V_N - V_P) +$ $D\cdot h(C_S - C_P) + \mu\cdot h\cdot\dfrac{C_S + C_P}{2}\cdot(V_S - V_P) +$ $D\cdot h(C_F - C_P) + \mu\cdot h\cdot\dfrac{C_F + C_P}{2}\cdot$ $(V_F - V_P) + D\cdot h(C_B - C_P) + \mu\cdot h\cdot$ $\dfrac{C_B + C_P}{2}\cdot(V_B - V_P) + h^3\cdot Source$ The terms of C are collected to form the matrix coefficients (Equ: 27)

$A_PC_P + A_EC_E + A_WC_W + A_NC_N + A_SC_S + A_FC_F + A_BC_B = B + A_{P0}C_p^{old}$ where:

$A_P = A_{P0} - h^3\cdot S_{proportional} + \sum_\alpha A_\alpha$ $A_{P0} = \dfrac{h^3}{\Delta t}$ 28) $A_\alpha = \begin{cases} D\cdot h & \text{no membrane at } \alpha \\ D_{membrane}\cdot h & \text{membrane at } \alpha \end{cases}$ $B = h^3\cdot S_{constant} + h^2\cdot\sum_\alpha Jm_\alpha + h\cdot\sum_\alpha B_\alpha$ $B_\alpha = \begin{cases} \mu z\dfrac{C_P + C_\alpha}{2}(V_\alpha - V_P) & \text{no membrane at } \alpha \\ \mu_{membrane}\cdot z\dfrac{C_P + C_\alpha}{2}(V_\alpha - V_P) & \text{membrane at } \alpha \end{cases}$ $\alpha = E, W, N, S, F, B$ Where chemical reactions are represented as a first order linearization $S_{constant}$, $S_{proportional}$ where Sp is constrained to be negative for stability reasons. Membrane reactions (in the context of species in solution) is represented by reactions with binding sites on the surface of the membrane, and as fluxes through the membrane. The binding site reactions are treated as in the above case (Sc and Sp). The fluxes are currently represented as some combination of a passive membrane term (defining an effective diffusion and mobility constant) and an arbitrary membrane flux term (Jm) to handle any non-linear terms.

The modeled chemical reactions include bulk reactions and membrane reactions. All bulk reactions are treated as coupled differential equations describing their reaction rates. Reactions are created such that their behavior is adjusted to interact only with their defined environment. The general form assumed is as follows:

29) $aA + bB \underset{k_{-1}}{\overset{k_1}{\rightleftharpoons}} cC + dD$

30) $-\dfrac{1}{a}\dfrac{d[A]}{dt} = -\dfrac{1}{b}\dfrac{d[B]}{dt} = \dfrac{1}{c}\dfrac{d[C]}{dt} = \dfrac{1}{d}\dfrac{d[D]}{dt}$ $= k_1[A]^n[B]^m - k_{-1}[C]^r[D]^s$ These relationships are true provided that there are no intermediate species, or if there are intermediates, their concentrations are independent of time for most of the reaction period. In general, the reaction rate for either elementary or multi-step reactions is a nonlinear relation that may be linearized about a set of current conditions.

31) $\dfrac{d[A]}{dt} = -f_{A\_linear}([A], [B], \ldots)\cdot$ $[A] + f_{A\_constant}([C], [D], \ldots)$ A particular simulation may not have defined one or more of the reagents as state variables. The reaction model must then either be disabled or simplified depending on which reagents are missing. A simplified model uses a constant concentration for each missing reagent as defined for that biological feature type. This constant concentration can be specified in the model description or the default value for that feature type will be used.

Figure 6:
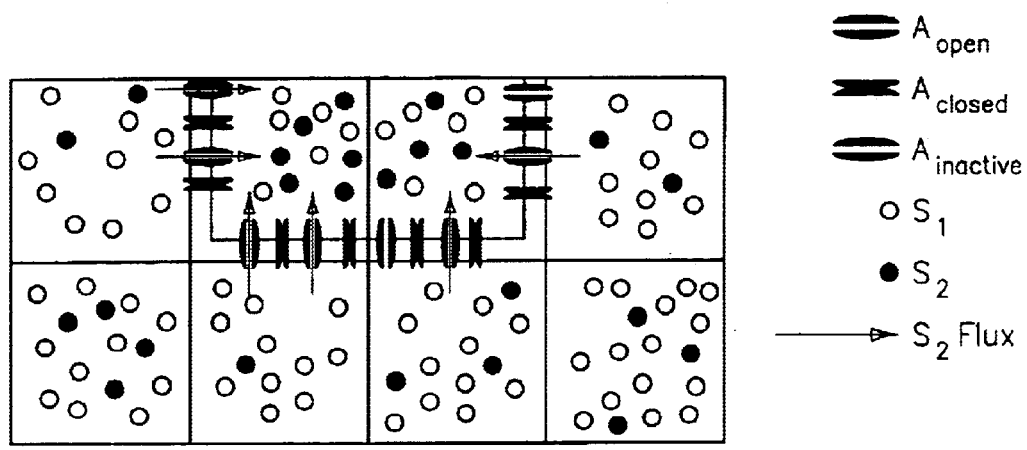
FIG. 6 is a diagram of typical membrane reactions and their corresponding molecular states.

All-membrane reactions are treated as coupled differential equations describing their reaction rates. These reactions, like bulk reactions, adjust their complexity according to the defined environment of the simulation. Typical membrane reactions are pumps and channels. Each membrane reaction requires a set of one or more corresponding molecules each representing a distinct configuration (state) of the corresponding pump, channel, or carrier (e.g. open, closed, inactive). FIG. 6 illustrates the modeling of the various membrane reaction states. A membrane reaction state represents a significant combination of bindings and conformations of a pump or channel needed to describe its dynamic behavior. This allows a model of channel or pump dynamics to incorporate discrete states such as open, closed, and inactive. The state transitions are defined in terms of reaction rate equations that can be functions of membrane potential and species concentrations on either side of the membrane. The equations are written such that the stoichiometry of the whole model is consistent and that flux is conserved.

These states are defined in terms membrane surface densities and can be represented by state variables or by constants. There is only one value of the surface density of a membrane variable that is defined for each element, although an element may have up to 6 separate membrane surfaces. Reaction rates on membrane variables (channels and pumps) are averaged over the membrane surfaces of an element. Missing reagents are handled in a manner similar to that of the bulk reactions defined above. An important additional requirement of the trans-membrane reactions is that flux be conserved.

Species on either side of a membrane can be effected by membrane reactions in two ways. The first is to pass through the channel or pump as membrane flux. The second is to react with a binding site on a membrane molecule, causing a membrane reaction state transition. These reactions are generally governed by the membrane reaction states, the potential difference across the membrane, and the concentrations of one or more species on either side of the membrane. Channels can in principle have receptor sites on either or both sides of the membrane. The conservation of flux can be used as one of the convergence criteria for the numerical solution.

The treatment of membrane channel and pump surface densities assumes a single value for each element, representing the average over all that element's membrane boundaries. This defines a single (average) concentration over all membrane surface patches connected to a single element. An alternative is to define two dimensional membrane patches. Thus, an element boundary that is associated with a membrane will reference that two dimensional membrane patch.

Figure 7:
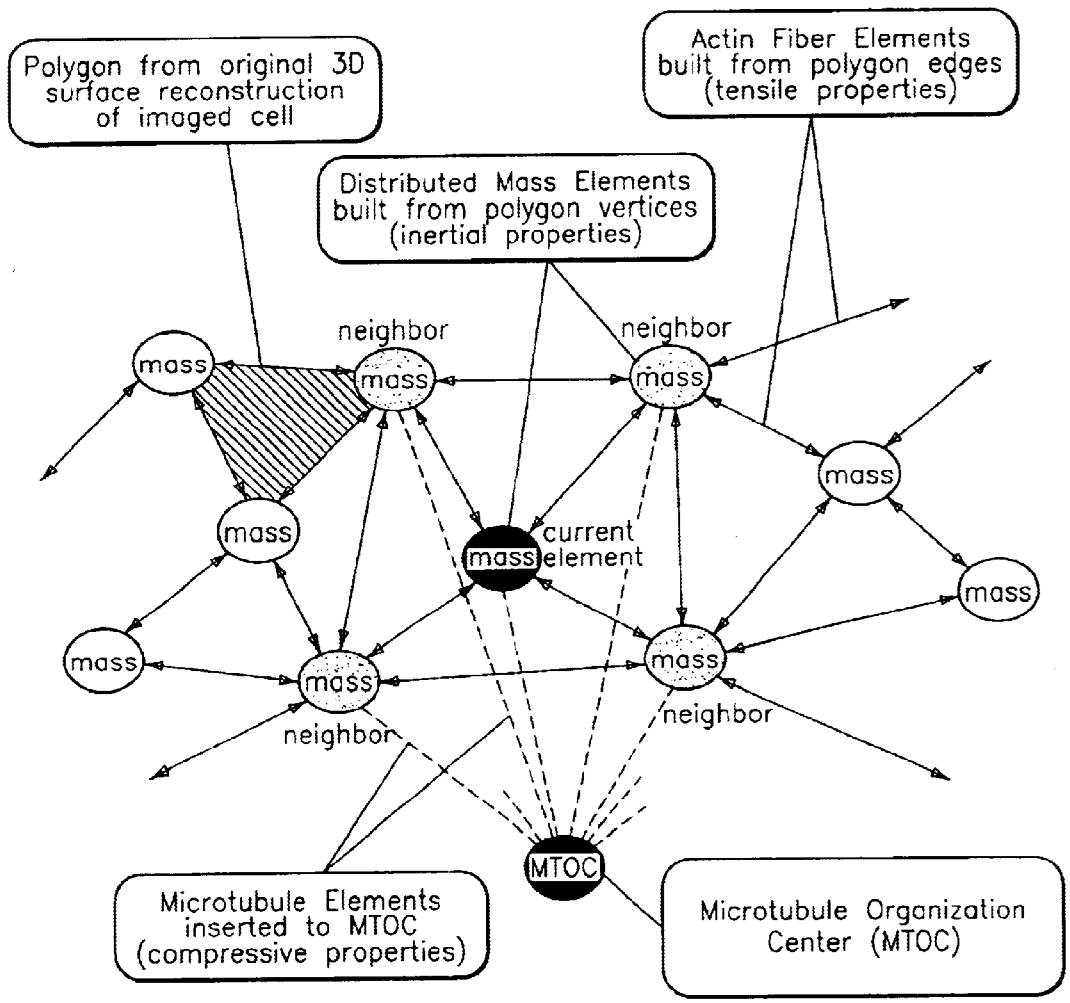
FIG. 7 is an illustration of mechanical simulation elements.

The modeling of mechanical dynamics requires a mesh of connected elements where each element interacts with its neighbors through applied forces and each element reacts according to applicable equations of motion. An exemplary simulation mesh is based on use of an iso-surface reconstruction. The corresponding mechanical model describes cell membrane movement as tensile, compressive and viscous forces acting on distributed inertial masses. FIG. 7 illustrates a polygonal mesh from a surface reconstruction of three dimensional data set of a cell which is used as the basis for a mechanical simulation of membrane characteristics. The geometry of the polygonal mesh is based on actual volume data. It is understood that the geometry of the surface model can be based on an iso-surface reconstruction of a three dimensional microscopy image, or any other polygonal surface model. Thus, the simulated polygonal surface can be rendered in three dimensions and compared with results from experimental micro-manipulation of the same cell. The mechanical dynamics can be with alternative techniques such as finite element analysis.

A large collection of reaction models will be necessary to support simulations of various cell lines and physiological problems. Membrane reaction models and local reaction models are maintained as reaction descriptions, which define the reaction rates of certain molecular species as a function of the local environment. Each description consists of a set of rate expressions that are functions of model variables and parameters (e.g. reaction rates, pump rates, etc.). These descriptions are stored in a database, and when needed, $C^{++}$ code is automatically generated to create a simulation specific model object library. This allows users to specify new models without any programming experience, and with little regard for the underlying numerical methods. In addition, upgrades of simulation software architecture will not affect the configuration management of reaction model descriptions.

A database of specific and customizable reactions and membrane mechanisms may be made available for building cellular models through a central repository. A naming standard for both models and molecular species must be created to allow models to be inter-operable. The selected models are then automatically combined to form a single reaction rate for each molecular species in each feature. These rates are automatically coded, compiled and linked with the simulation framework. A user could access the repository to retrieve the customizable simulations of reactions and membrane mechanisms. The user the combines these components to form the cellular model.

When building an integrated cellular model from an arbitrary collection of individual reaction models, care must be taken to achieve a consistent initial condition. Many simulations take the form of homeostasis (steady state) perturbed by some stimulus (system input). It is generally beneficial to separate the forced response of the simulation (response due to the input) from the natural response of the simulation (response due to the initial conditions with no input). To look at the forced response (of most interest), the initial conditions should be balanced such that all of the variables are set to appropriate steady state values. This is generally not a trivial task for a newly generated collection of individual models with user defined initial values of molecular species and potential.

The approach taken to address this issue is a constrained optimization of model and feature parameters. Model parameters include individual reaction rates, binding rates, pump flux constants or any "constant" used to describe the dynamics of the modeled mechanism. Feature s include initial concentrations of molecular species, surface densities of membrane species, and electric potential defined for that feature. Any parameter is described in terms of a probability distribution over its allowable values. For a particular application, if a parameter is perturbed from its most probable (nominal) value, then a penalty function is evaluated. This penalty is generally inversely proportional to it's normalized probability distribution. An overall penalty function is generated as a weighted sum of individual penalty functions, where the weights are determined by the users, and reflect the confidence in the accuracy of each parameter's distribution.

A non-linear optimization is performed to minimize the steady state net reaction rates and fluxes while also minimizing the total penalty function. This optimization process is interactive, allowing the user to update confidence and distribution functions such that the simulation best matches the desired physiological situation. This allows homeostasis to be achieved in an orderly fashion with the tradeoffs being driven from the user's experience and knowledge. In an exemplary embodiment, the invention uses a conjugate gradient search algorithm to find the local minimum based on initial parameter values. A more robust algorithm may incorporate a Monte Carlo method of generating the initial parameter space vectors such that the best local minimum may be comparable to the global minimum.

The simulation framework can periodically store the values of the state variables to files called simulation dumps. Each simulation dump uniquely represents the simulated physiology at a discrete point in time. Any state variable can easily visualized over space and time using tools that are compatible with the simulation dump files.

In addition to state variables, the models can be used in the post-processing of the data to determine some derived states. Derived states are reaction rates, fluxes, or anything else that can be expressed in terms of the state variables. Which means, by the definition of state variables, that anything that is represented in the models can be reconstructed after the simulation via the simulation dumps. This enables a very flexible post-processing capability. This capability is enabled by the software architecture, which is object oriented and very modular such that these questions can be asked within the framework without making the individual models complex.

Geometric models and simulation elements can both be displayed within an integrated 3D viewer. The model can be displayed as a set of polygonal surfaces that can be quickly manipulated with accelerated graphics. The state variable values within the simulation elements are then volume rendered into the same scene as the surface model. A more general multivariate, four dimensional data analysis package is needed to properly analyze the data.

The simulation results are currently associated with the model description and a simulation log file. A database of either containing or citing simulation models, results, and conclusions would be very helpful in the process of cooperative research. In this way, individual and aggregate models and their associated parameters can be evaluated, and confidence in parameter usage can be determined. This type of situation will work well if users make their results freely available to others.

Figure 8:
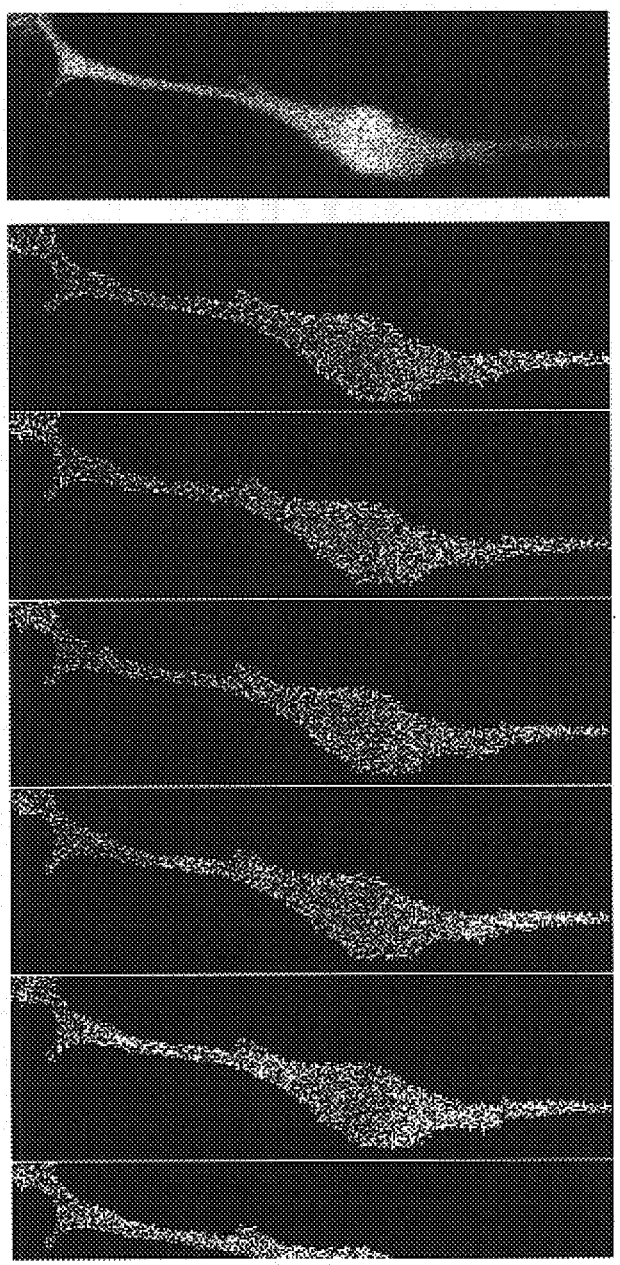
FIG. 8 is a series of images of an actual cell.
Figure 9:
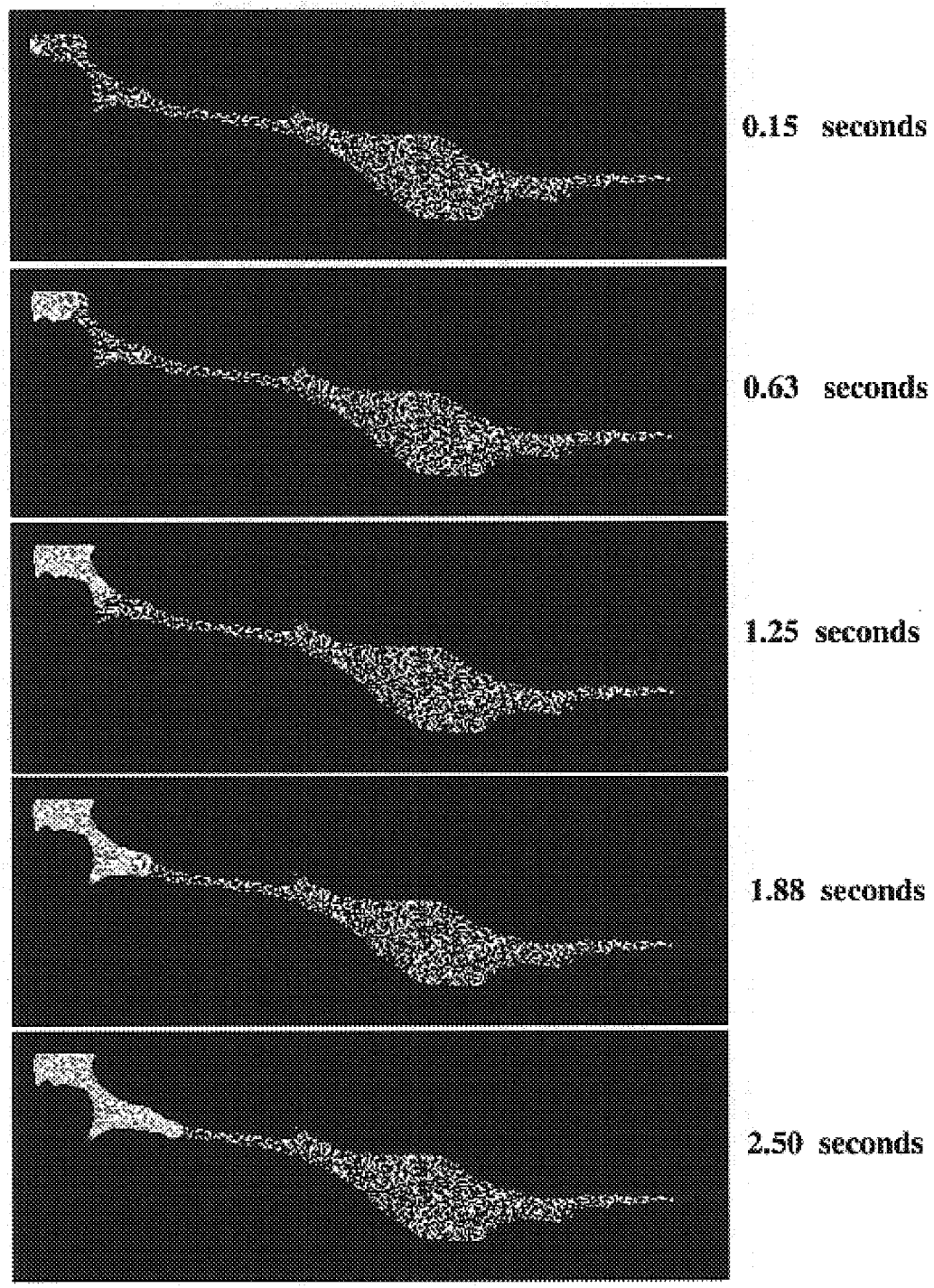
FIG. 9 is a series of images of a simulated cell corresponding to the actual data in FIG. 8.

Example simulations have been generated involving the calcium induced calcium dynamics involving the IP3 receptor in neuroblastoma cells. FIG. 8 is a time series of experimental images of mouse neuroblastoma loaded with a calcium indicator. The images shown in FIG. 8 are two dimensional slices of a fluorescence microscopy image of the cell. The concentration of calcium was image at regular intervals during an experiment designed to observe calcium dynamics. FIG. 9 is a series of simulation images corresponding to the actual images shown in FIG. 8. FIG. 9 shows a series of two dimensional slices of a chemical simulation volume. The simulation modeled a wave of increased free calcium ion concentration due to intracellular triggering event. Because the simulation geometry was generated based on the actual cell image, the simulation data of FIG. 9 is easily compared to the experimental data shown in FIG. 8. The model geometry was taken directly from a microscope image of the cell in question, and the model was built with a collection of individual models of physiology from the literature.

Figure 10:
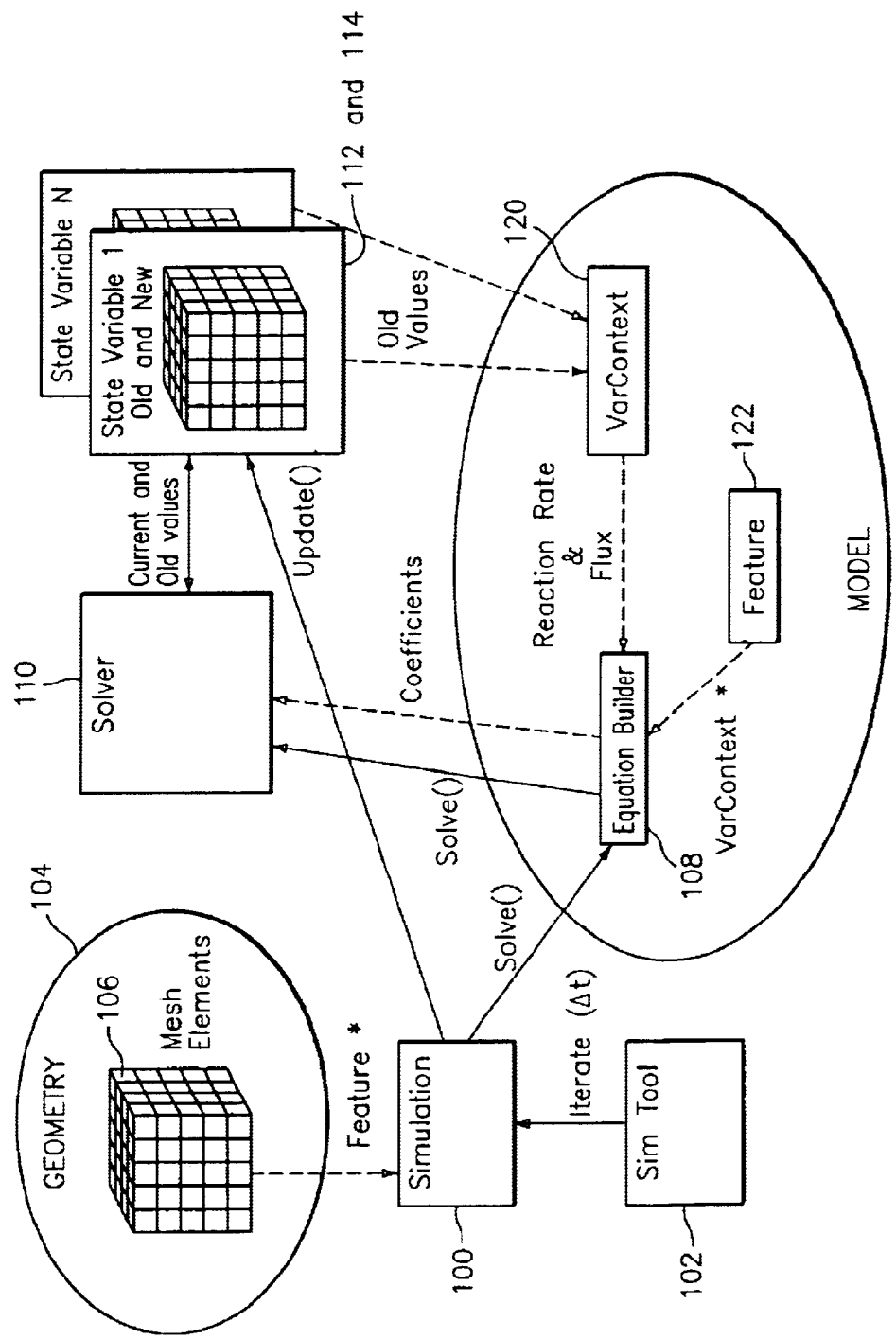
FIG. 10 is a control flow diagram for the simulation.

FIG. 10 is a flow control diagram illustrating a number of modules that combine to form a simulator that implements the simulation. The simulation may be implemented on a general purpose computer or in dedicated hardware having software (firmware) associated therewith or a combination of software and hardware. As shown in FIG. 10, a simulation module 100 controls the progress of the simulation. The simulation module 100 controls the timing of the simulation and transfers data to and from other portions of the simulator and provides overall control for the execution of the simulation. The simtool module 102 receives user commands and provides the commands to the simulation module 100. A simulation mesh 104 is a three dimensional array of simulation elements 106. The simulation elements 106 are each associated with a feature object 122 which identifies the physiological features of the simulation element 106. Current state variables 112 and past state variables 114 are stored and are provided to a solver 110, along with information from the equation builder 108 to update the state variables of the simulation. The solver 110, the equation builder 108 and the state variable storage 112 and 114 are all connected to the simulation module 100 for control purposes. The varcontext module 120 maintains the reaction rates for a specific species and is referenced by the cellular feature 122. For example, if the simulation element 106 corresponds to cytoplasm then the simulation element 106 is linked to a feature 122 corresponding to the cytoplasm. The varcontext module 120 stores the net reaction rate for a particular variable for the cytoplasm. In this way, the user knows which reactions may be simulated for a particular cell feature and time is not wasted searching for available reactions.

The simulator shown in FIG. 10 first initializes the simulation by performing the following operations.

determine initial iteration time load default values into variables initialize variable contexts if applicable, calculate charge and initialize potential Upon each iteration of the simulation, the simulation framework performs the following operations.

do the following until maximum normalized error <1 or max iterations reached.

(a) for each variable, do the following
    (1) for each element, do the following
      (i) get feature
      (ii) get corresponding varcontext data
      (iii) ask for reaction rates and fluxes for current variable at current element
      (iv) form coefficients based on equation builder
    (2) solve implicit matrix equation for PDE's or explicit ODE equation
  (b) if potential defined, solve for potential using equations 8 and 9
  (c) update variable values.

An alternative embodiment of the invention will now be described. In the alternative embodiment, feature models are mapped to regions in the n-dimensional description of the biological material. A number of mapping methods may be used which are disclosed in detail herein. The regions are then decomposed into computational sub-domains, each of which is linked to a model which represents the physiology of the region. This implementation is similar to that described above, but provides for a variety of representations of the biological material.

As described above, the models may include feature models representing the physiology (e.g., material properties and species interactions) within cellular compartments and structures (e.g. ER, cytosol), reaction or function models representing chemical reactions and molecular motion (e.g. enzyme kinetics, receptor binding, membrane fluxes) and species models representing molecular species (e.g. calcium, ATP). These models, when combined with a specified cellular geometry, are sufficient to fully describe any chemical dynamics simulation implementation.

The physiological models represent fundamental cellular physiology in a way that is independent of the mathematical formulation and the numerical implementation. A single physiological model can be mapped to various mathematical formulations in multiple ways. A first approach maps a model to mathematical formulations based on different levels of complexity ranging from the Nernst/Plank equations with spatially resolved potentials defined on a three dimensional domain, to a simple compartmental representation of reactions and fluxes with homogeneous species and no potential. Alternatively, models can be mapped to mathematical formulations based on average or individual behavior.

The species category of models includes species models and membrane species models which represent molecular species that are either in solution or membrane bound, respectively. These species can be represented as continuous concentrations and fluxes of molecular species, or in terms of discrete events (including reactions and motion) acting on individual molecules. For individual molecular representation, the state of each particle includes its location, unique molecular conformation and whether it is bound to a structural feature. The species models identify molecular species, and are classified as being either membrane species or volume species. The membrane species are described by a surface density of the molecular species for each feature that contains a membrane. The volume species are described by a concentration and a diffusion constant. The mapping of species category models to mathematical implementations is summarized in Table 3.

TABLE 3

Species Model Implementation Mapping

| Model Abstraction | Implementation | State Information |
|---|---|---|
| Species | continuous | For each volume element: |
| valence | concentration | concentration |
| average | discrete | For each particle: |
| concentration within each feature compartment | particle | location (volume element index) bound structural species (if any) |
| Membrane Species | continuous surface density | For each membrane element: surface density |
| average surface density for | discrete membrane | For each particle: |
| each feature membrane | molecule (channel, pump) | location (membrane element index) state (molecular conformation) |

The category of models that corresponds to general anatomical features includes feature models and structural feature models. Feature models represent abstractions for spatially discrete physiological components of the biological material. The feature models provide a topological representation of the physiology of a portion of the biological material. The feature models lack spatial information and can be mapped to a variety of spatial representations or regions. A first type of mapping is spatial mapping in which the feature is mapped to one or more spatially defined regions in the biological material. For example, the feature model for a nucleus may be mapped to one or more spatially resolved nuclei in the biological material. Another type of mapping is distributed mapping in which a feature is mapped as a fraction of the region corresponding to its topological parent. Topological parent refers to a feature model that encapsulates the feature model in questions. For example, ER can be mapped as being distributed throughout the region corresponding to the cytosol. Another type of mapping is compartmental mapping in which each feature is mapped to a respective single region without spatial information (e.g., zero spatial dimensions). Interaction between regions is represented by coupling models for separate regions but spatial information is not required. This is often referred to as compartmental modeling.

The feature models contain species and a collection of reactions or functions that describe the biochemical behavior of that feature. Structural feature models represent boundary features whose physical properties can constrain the motion of molecular species, for example membranes and cytoskeletal structures. A feature model can correspond to a spatially separated computational subdomain or approximated as a continuously distributed element within another feature (e.g. endoplasmic reticulum approximated as continuously distributed within the cytosol). A structural feature can represent cytoskeletal components (e.g. microtubules) as directed contours that may be mapped as an ordered list of one dimensional elements onto the same volumetric mesh. A structural feature representing a membrane is represented spatially as the boundary between the regions of the corresponding feature models (e.g. ER membrane resides between the ER and cytosol). Membranes can be implemented as a list of elements that can be indexed by the neighboring volumetric elements, and can constrain motion, permit flux and binding to membrane bound species. Average geometric information, such as surface to volume ratios for the appropriate feature complete the necessary information for a single point compartmental simulation. The mapping of feature models to mathematical implementations is summarized in Table 4.

TABLE 4

Feature Model Implementation Mapping

| Model Abstraction | Implementation (After Geometry is Specified) | Domain Representation |
|---|---|---|
| Feature Model | spatially resolved | for each compartment: |
| reaction, membrane reaction, and free motion models value of membrane potential volumetric conductance membrane capacitance | 1 or more spatially resolved volume compartments membrane is interface between dissimilar compartments | each interior is represented as a region of contiguous volume elements. each membrane is represented as a set of membrane elements between compartments |

TABLE 4-continued

Feature Model Implementation Mapping

| Model Abstraction | Implementation (After Geometry is Specified) | Domain Representation |
|---|---|---|
| | continuously distributed | interior is represented as a volume |
| | distributed compartment represented as volume fraction of enclosing feature membrane is distributed surface | fraction of enclosing compartment membrane represented as a distributed surface. species and membrane species must be uniquely identified because of feature collocation membrane fluxes are converted to average volumetric rates. |
| Structural Feature Model | discrete only | for each structure: |
| constrained motion models number of bound particles | (e.g. microtubule, microfilament, membrane) location | ordered list that maps volume elements to structure |

The category of functional models that corresponds to general physiological mechanisms includes reaction models, membrane reaction models, motion models, and constrained motion models. Reaction models represent the abstractions for chemical reactions occurring 'in solution', and can be mapped to a deterministic reaction rate, or a reaction probability, depending on the context of the species involved (concentrations or individual molecules). Reactions are collections of related membrane reaction steps (e.g. membrane receptor binding), volume reaction steps (e.g. calcium buffering), and membrane fluxes (e.g. flux through an ion channel). The fluxes and reaction rates are represented by arbitrary algebraic expressions. These expression objects are capable of basic algebraic simplification, partial differentiation, and binding to the appropriate parameters and species, and numeric evaluation.

Membrane reaction models represent the abstractions for chemical reactions occurring 'in a membrane', and can either be a deterministic reaction rate and related continuous flux, or a reaction probability and flux probability, depending on the context of the reactive species (concentrations or individual molecules) and of the membrane transported species. Motion models represent the abstractions for diffusion or electro-diffusion, as well as diffusion within an externally applied electric field, and can either be described by the associated partial differential equations (Fick's Law) or by a random walk of individual particles, depending on the species considered (concentration or individual particles). Constrained motion models represent the abstractions for motion of species that are attached to a structural feature (such as an RNA granule attached to a microtubule). Such motion manifests itself as a random or directed motion that is constrained to follow the geometry defined by the corresponding structural feature model. The mapping of functional models to mathematical implementations is summarized in Table 5.

TABLE 5

Functional Model Implementation Mapping

| Model Abstraction | Implementation | Function |
|---|---|---|
| Reaction Model | Continuous | reaction rate equations |
| reaction rate constants reactants products | Mass action kinetics Discrete Stochastic description of reactions involving single particles including capture of particles to structural features | transition probability using a continuous time Markov process |
| Membrane Reaction Model | Continuous | reaction rate equations |
| reaction rate constants reactants products flux equations Motion Model | Rates are function of conc. Discrete Transition probability defined for pair of possible reactants Continuous | flux equations transition, flux probability using continuous time Markov process Fick's Law or |
| species diffusion coefficient or expression mobile species | Diffusion in terms of concentrations and electo-migration in terms of field | Nernst/Plank Equation |
| | Discrete Stochastic motion of discrete particles with or without "drift" | random walk with or without drift |
| Constrained Motion Model | Discrete only | constrained motion along |
| statistical rates of motion species structural species | Stochastic motion of discrete particles constrained to bounds of structures | structure (either random walk with drift, or specified velocity) |

The chemical dynamics of discrete particles can include reactions with other discrete particles and reactions with continuously defined species (concentrations). Reactions with continuous species will occur in a quantal manner and will conserve the stoichiometry of the reaction. The motion of a discrete particle may be described in terms of a three dimensional random walk, capture to a discrete structure, and directed motion along that structure. Both the motion and chemical dynamics of these particles and structures will be formulated in terms of stochastic discrete events, and integrated with the continuous reaction-diffusion description.

The model mapping represented above facilitates parameter estimation activities for individual simulation models. Once model parameters are defined for various applications, a knowledge base for the coherent representation of theoretical models and experimental results can be generated. Creation of a knowledge base of models will result in efficient wide scale reuse and generalization of physiological models.

The information associated with model parameters includes experimental constraints, model structure constraints, and model behavior sensitivities. The experimental constraints encapsulate results of low level biochemical experiments where measurements, and their accompanied uncertainties, reveal ranges of allowable parameter values or relationships between model parameters. The model structure constraints consist of those constraints that result from the relationships defined by the model structure (such as relationships between kinetic and equilibrium constants of a reaction). The model behavior sensitivities are the sensitivities of each output (or state trajectory) to perturbations in parameter values.

The result of a model sensitivity analysis can be augmented by forming a list of relationships between independent states and their associated important (most sensitive) parameters. The dependence of important functions of states (e.g. fluorescence of a calcium indicator) on parameters can also be evaluated. The primary sensitivity functions for the sensitivity of the states to each parameter over the temporal and/or spatial domain are represented. Additional derived sensitivities (for instance to derived outputs, such as aggregate features like period, maximum amplitude, relaxation time) may benefit the modeler. Local sensitivity analysis with respect to states (and functions of states) may be calculated for steady states and for state trajectories. The model sensitivity provides an objective criteria for validating model goodness.

In addition to the species, feature and function models described above, the system may include geometry objects represent the cellular geometry (based on segmented images) and can be mapped directly to the corresponding cellular features. The geometry can currently be specified as any n-dimensional spatial representation (e.g., 2-D or 3-D segmented images) with the appropriate scaling information to properly define a simulation domain.

Simulation context objects may be used to represent the context of a particular simulation as a specific mapping of the model objects to the geometry objects. This mapping specifies the species and reactions present in each feature within the corresponding region in the geometry. With the addition of initial conditions and boundary conditions for each species, a particular simulation is completely specified. This context specifies the generation of the ordinary and partial differential equations of the system. The computational mesh (e.g., structured or unstructured) is sampled from the geometry. These equations are represented symbolically within the modeling framework using expression objects.

For simulation of compartmental models (single point approximation), the appropriate ODEs are generated, and passed to an interpreted ODE solver (within the client applet discussed below with reference to FIG. 11). For the solution of a complete spatial simulation, the simulation context is sent to the remote simulation server where the corresponding code (e.g., C++) is automatically generated, compiled, and linked with the simulation library. The resulting executable is then run and the results are collected and stored on the server. The simulation data server then coordinates client access to the server-side simulation data for display and analysis.

Figure 11:
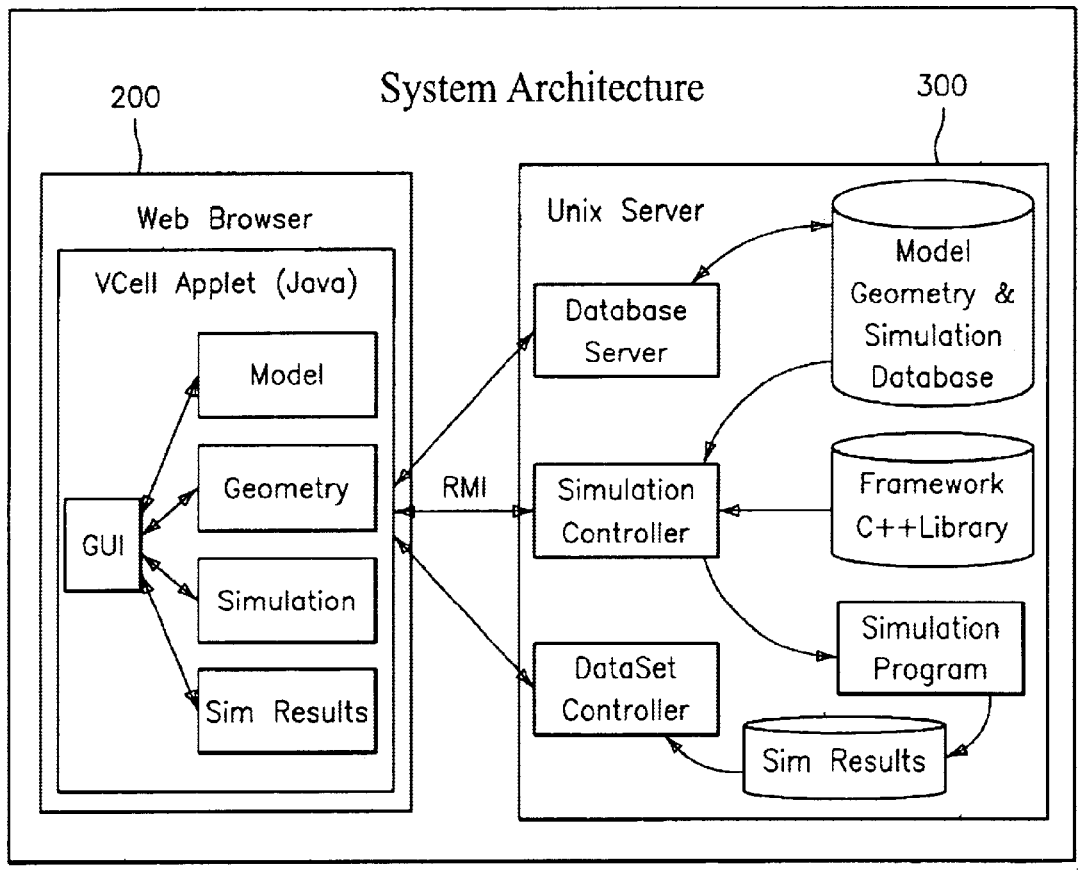
FIG. 11 is a block diagram of an exemplary system architecture.

FIG. 11 is a block diagram of a system architecture in an exemplary embodiment of the invention. As shown in FIG. 11, the system uses a distributed architecture. The system is decomposed into an application framework 200 and system server 300. The application framework 200 includes a graphical user interface (GUI) which allows the user to specify modeling parameters. The system server 300 include a database server, simulation controller (which encapsulates the simulation library), and the simulation dataset controller. The architecture is designed such that the location of the user interface in application framework 200 and the corresponding server 300 are transparent to the majority of the application. The typical configuration for the application framework 200 is a Java applet running in a WWW browser. The database server, simulation controller, and the simulation dataset controller are executed on a remote machine. The application framework 200 and server 300 are coupled via a network such as a LAN or the Internet. Alternatively, the software may be executed as a standalone application on a local machine with the requirement that the Java Runtime Environment and a C++ compiler are installed.

Figure 12:
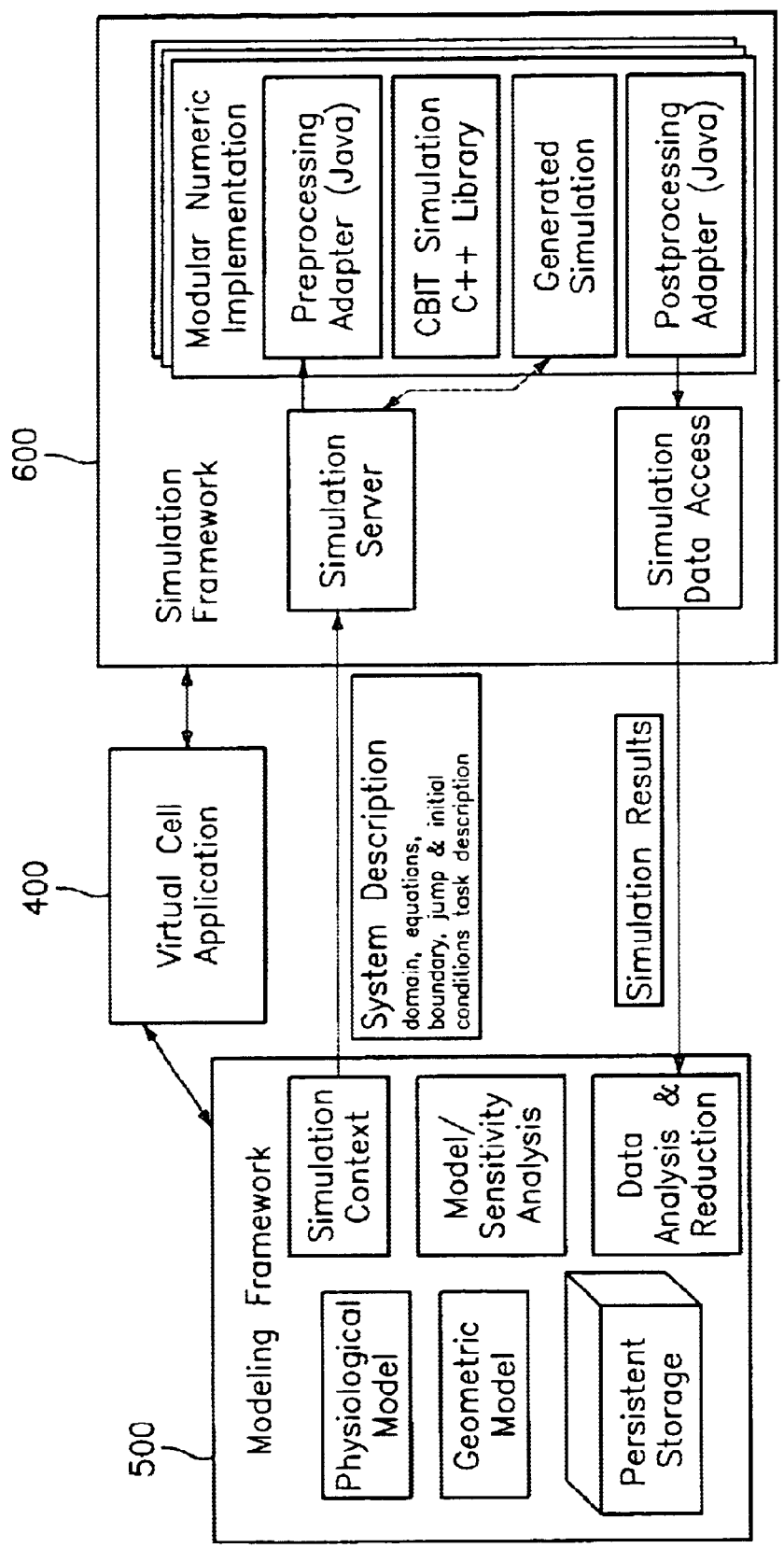
FIG. 12 is a block diagram of another exemplary system architecture.

FIG. 12 is a block diagram of an alternate system architecture. Aspects of the system may change as the system is used. The representation of physiological models will evolve as new modeling techniques and requirements are developed. The numerical codes applied to the simulation and sensitivity equations should be modular to take advantage of new methods, and third party numeric packages may be integrated for particular classes of problems (e.g. optimization). To support adaptability, it is beneficial to segment the system in a way that isolates the effect of these changes. FIG. 12 depicts a system architecture in which the system application 400, containing the user interface, is separate from a modeling framework 500 and a simulation framework 600. The modeling framework 500 allows the user to specify modeling parameters such as reaction rates. The simulation framework 600 executes the simulation and the returns the results to the modeling framework 500. This architecture encapsulates the complexity of detailed interactions between related components while providing stable, higher level, external interfaces for each component. The resulting framework has a logical separation of internal and external interfaces. A carefully designed framework can support adaptability of different implementations and new functionality with minimal impact to the rest of the system.

The modeling framework 500 and the simulation framework 600 interact with the system application across client/server boundaries to maximize performance and minimize network traffic. The distributed object technology may be CORBA (Common Object Request broker Architecture), which is the open industry standard for distributed objects and related services. This type of architecture hides the location of object services (such as simulations), allowing all objects to be local (client machine) or distributed over a network (e.g., LAN, Internet) as appropriate. For example, the current system application 400 may use a lightweight object request broker (e.g., JAVA RMI) and can be run as client/server or standalone with the exact same code. A testing interface may be included for the simulation framework 600 such that the end-to-end correctness of the code generation and the subsequent numerical solutions can be verified against exact and constructed solutions. This enables the maintenance of a comprehensive, system level test suite in the presence of an evolving computational framework.

The user interface 400 in an exemplary embodiment is a distributed Internet application written in Java programming language. The Java programming language has the advantage of running on virtually every platform in use, so users anywhere will have access to the system capabilities. The Java programming language has built in support for networking, database access, and distributed objects (server-side processes). Extensive use of software components (e.g., Java Beans) is employed to reduce development time by leveraging available third party visual components (such as graphs) and supply well defined interfaces for collaborative software development.

Both system architectures in FIGS. 11 and 12 utilize a database of physiological models, simulations and results. Database functionality provides for reliable persistent storage, privacy for unpublished information (e.g., proprietary models), and the ability to query for reactions and whole models. The models, simulations, and results may be stored in an external relational database using JDBC connectivity to a central server.

Figure 13:
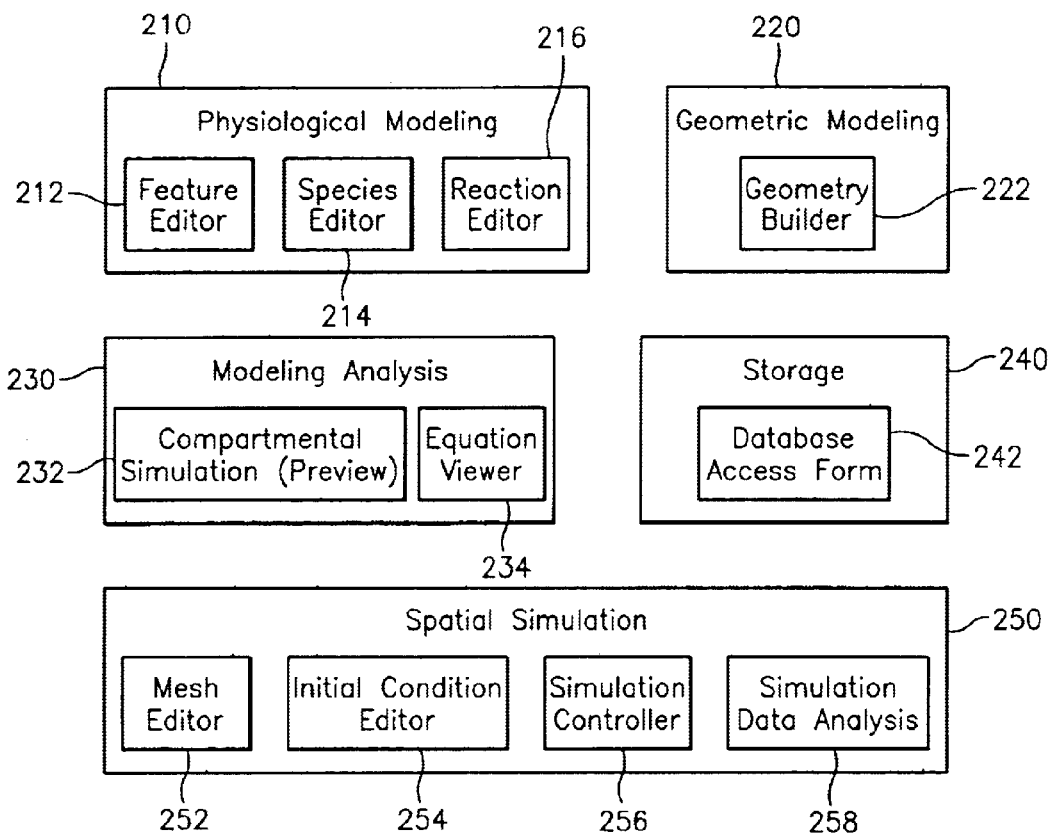
FIG. 13 depicts the organization of an exemplary user interface.

The user interface (for use with the system architecture of either FIG. 11 or 12) is described in further detail with reference to FIGS. 13–25. FIG. 13 depicts modules accessible through the user interface including a physiological modeling module 210, geometric modeling module 220, modeling analysis module 230, storage module 240 and spatial simulation module 250.

Figure 14:
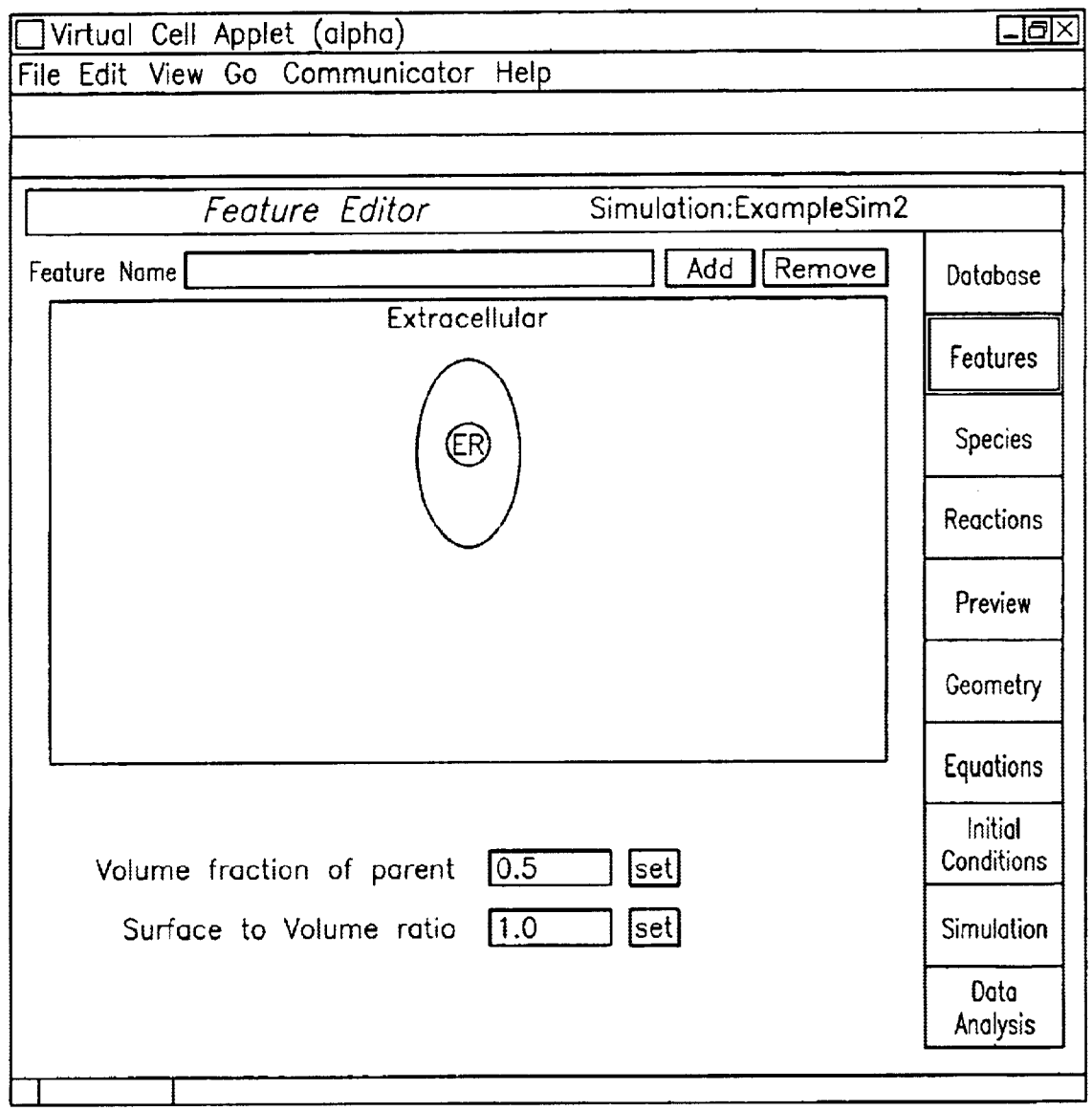
FIGS. 14–25 depict exemplary interfaces with modules of the system.
Figure 15:
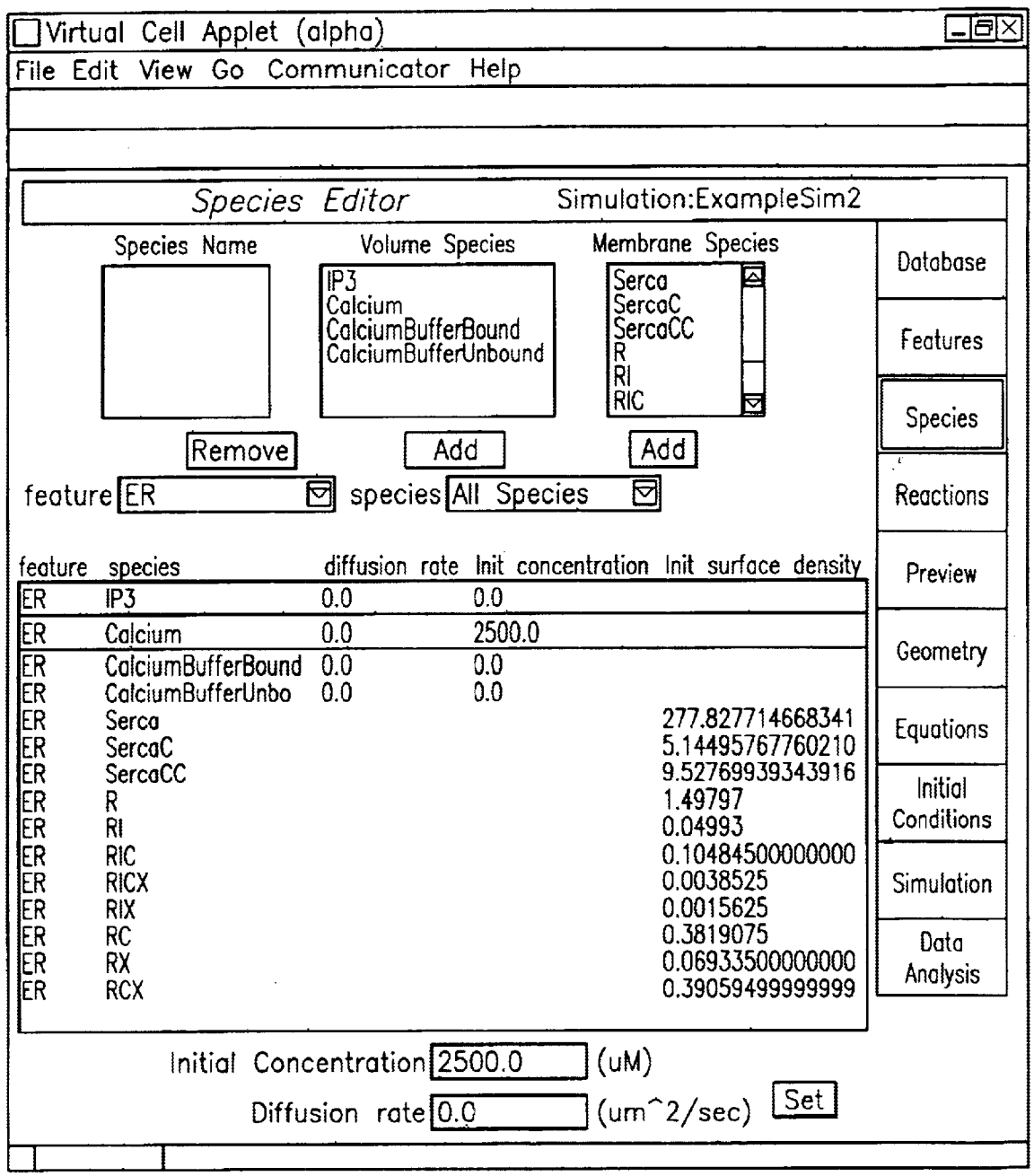
Figure 16:
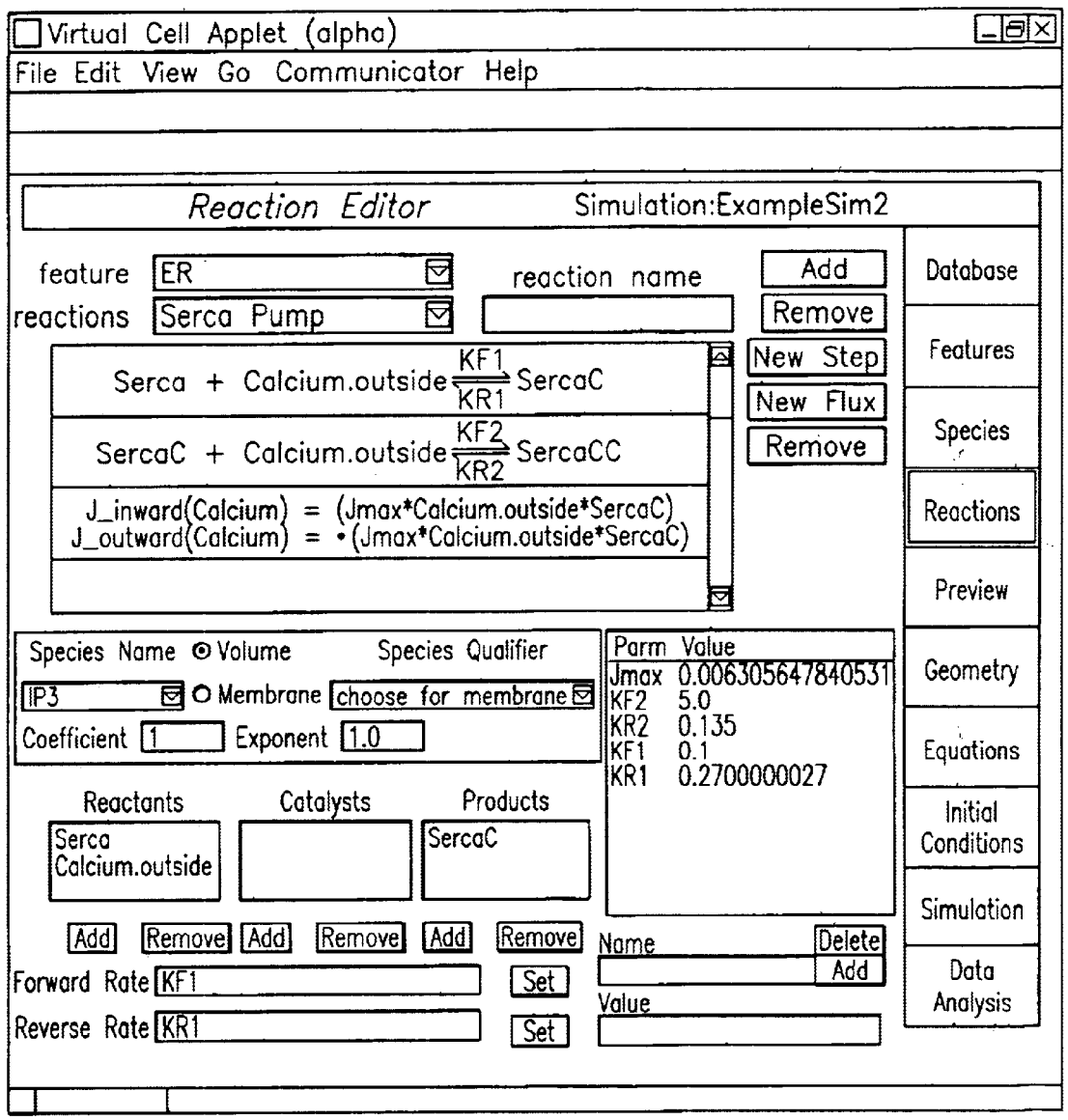

The physiological modeling module 210 includes a feature editor 212 that allows the specification of cellular features that represent the concept of topological compartments (e.g., ER lumen and ER membrane) within the cell model under study. The basic hierarchical structure of these features determines the case when one or more features are enclosed by another feature. The specification of average spatial properties of an enclosed feature (surface to volume ratio and volume fraction of enclosing feature) provides a complete description of a compartmental model. This is useful in calculating quick approximate solutions. FIG. 14 depicts an exemplary interface with feature editor 212. The species editor 214 allows the user to specify the volume and membrane species of a model. The default initial concentration and diffusion rates are specified to volume species within each feature. The initial surface densities of the membrane species are specified for each feature. FIG. 15 depicts an exemplary interface with species editor 214. The reaction editor 216 permits the user to define reaction models. A reaction model is composed of a series of simple reaction steps including any combination of volume reaction, membrane reaction, and flux reactions. FIG. 16 depicts an exemplary interface with reaction editor 216.

Figure 17:
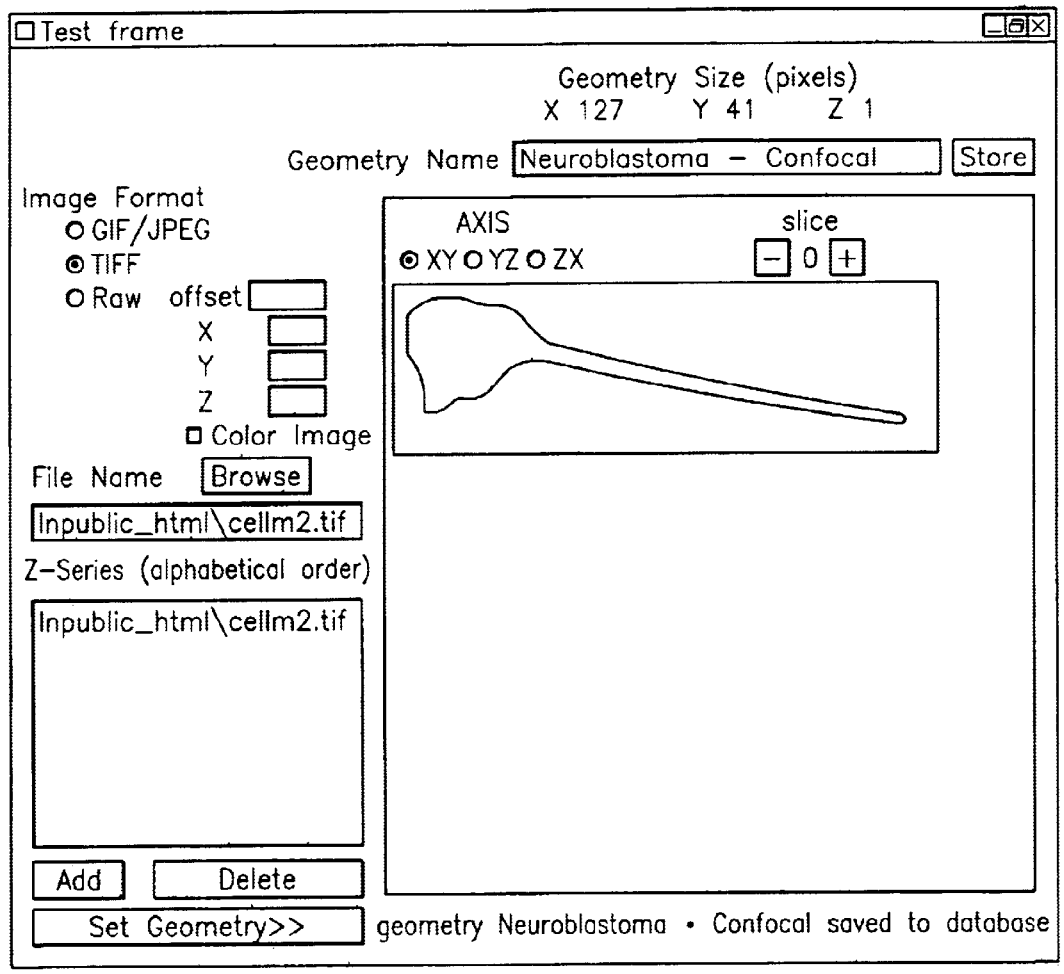

The geometry modeling module 220 includes a geometry builder 222 which is a standalone application that permits the construction of n-dimensional cellular geometric models based on a variety of sources (e.g., image files). The geometry builder 222 may be executed as a signed applet (trusted by the browser) or as a standalone application which does not have the same restrictions. The geometric modeling module 220 may enable capture of original images as well as the currently supported segmented images, and may include a simple segmentation tool (e.g. threshold). A simple geometry construction editor may also be used to specify artificial geometry. FIG. 17 depicts an exemplary interface with geometry builder 222.

Figure 18:
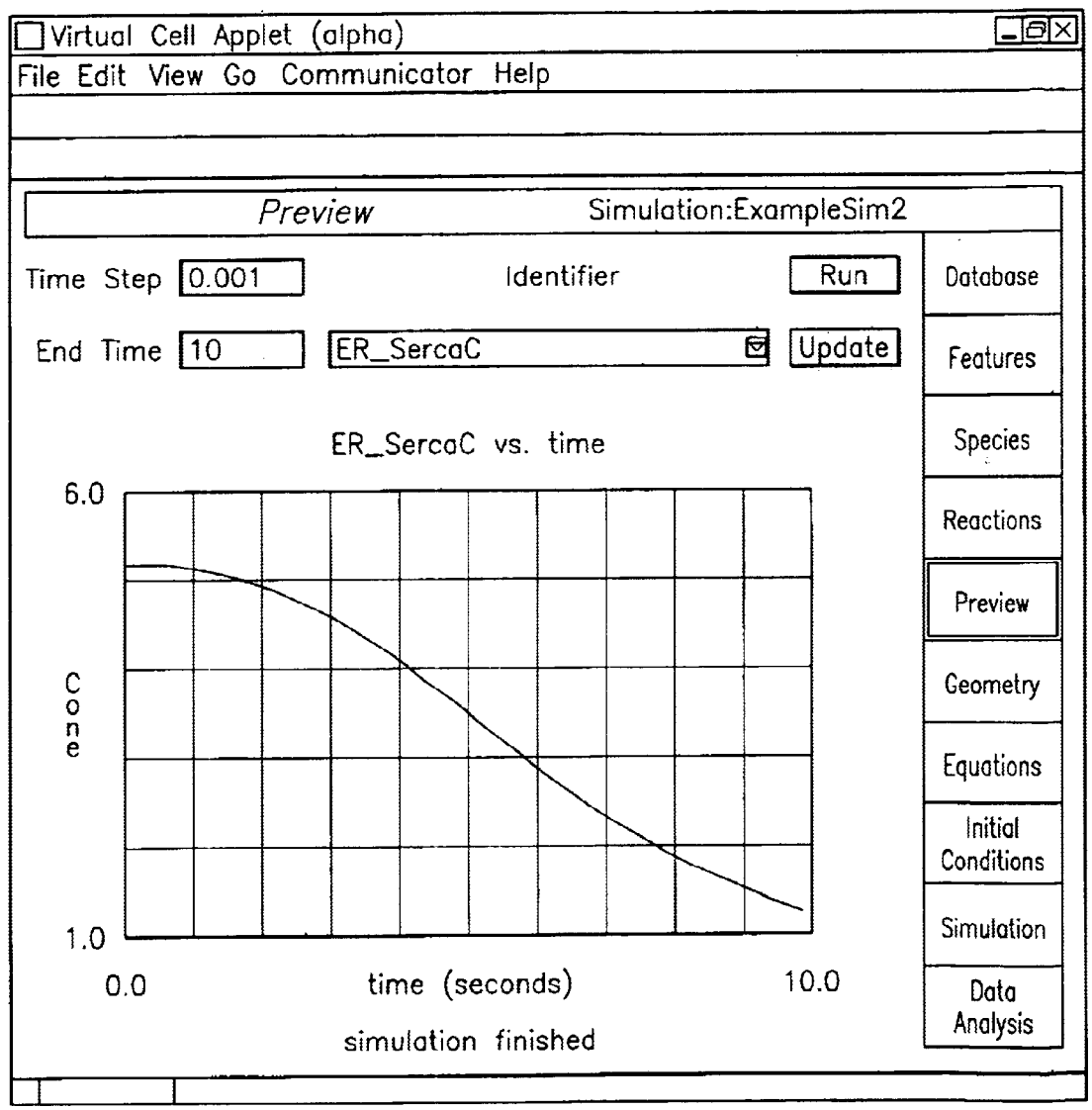

The modeling analysis module 230 includes a compartmental simulation component 232 which executes a compartmental (single point) simulation based on the defined physiological model and the geometric assumptions entered in the feature editor 212 (surface to volume ratios and volume fractions). This results in a set of nonlinear ordinary differential equations that typically are solved in seconds. This allows an interactive, though manual, modification of parameters and a quick determination of the effect over time. Once the simulation is complete, each species can be viewed easily. FIG. 18 depicts an exemplary interface with the compartmental simulation component 232.

Figure 19:
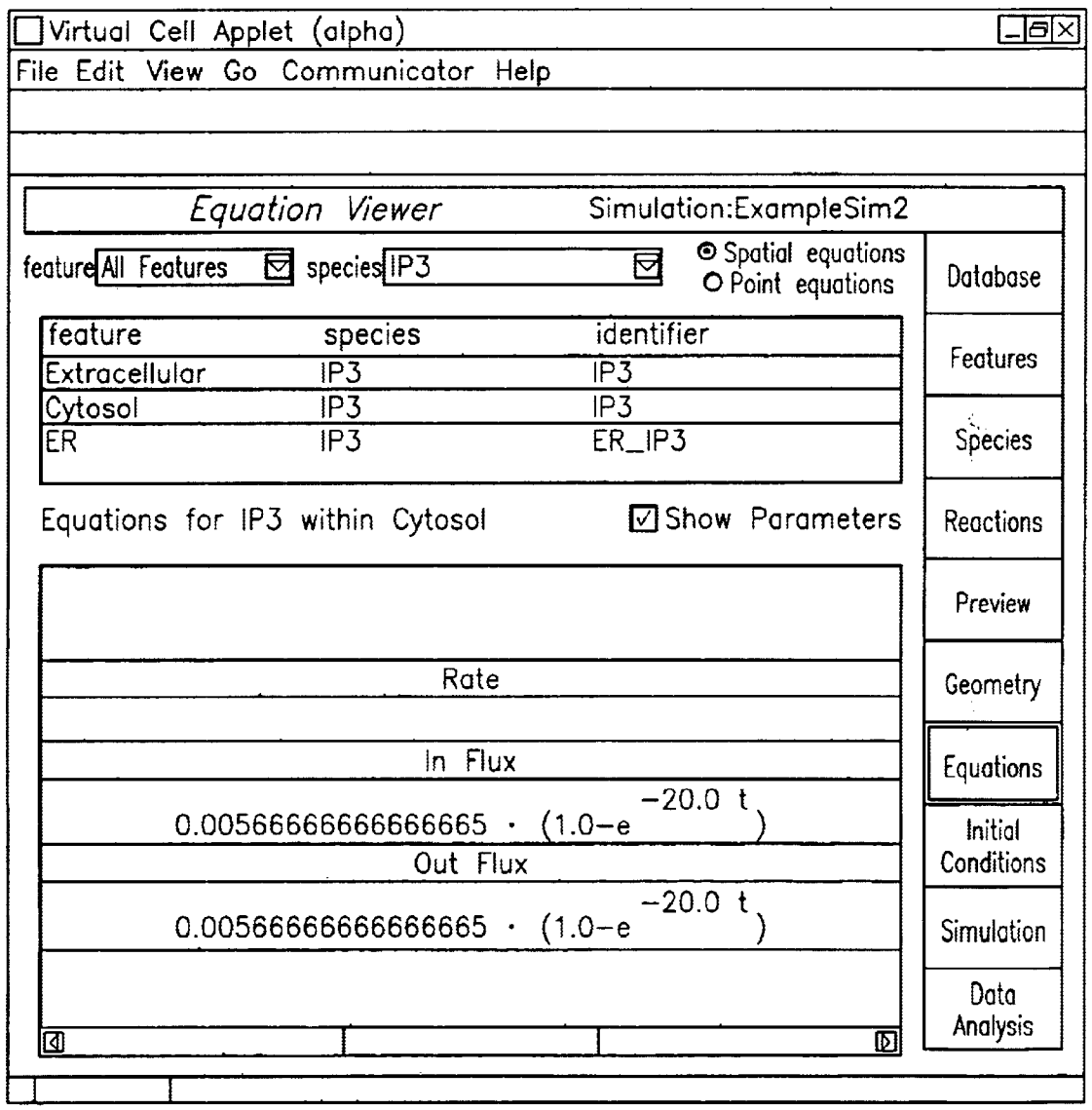

The modeling analysis module 230 includes an equation viewer 234 which displays the equations generated as a result of mapping the physiological model to either a cellular geometry model (spatial simulation) or a single point approximation (compartmental model). The parameter values may substituted (and the expression simplified), or left in their symbolic representation. FIG. 19 depicts an exemplary interface with the equation viewer 234.

Figure 20:
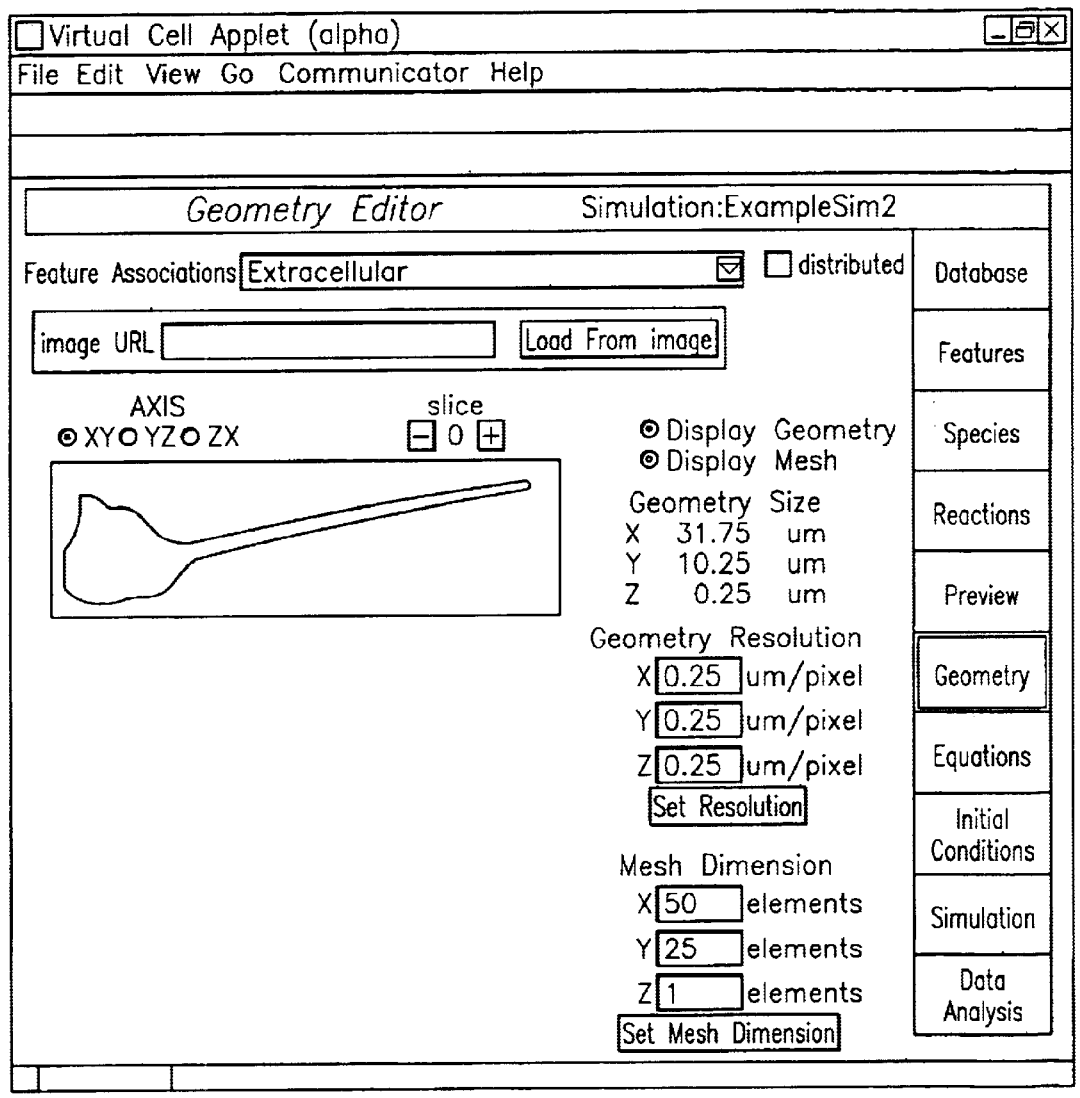

The spatial simulation module 250 includes a mesh or geometry editor 252 which allows some participation in the choice of spatial resolution of the simulation elements, thus considering the computational costs and the goodness of geometric representation. This interface directs the binding of regions of the segmented geometry to the corresponding features within the physiological model. An orthogonal mesh is specified and displayed interactively. FIG. 20 depicts an exemplary interface with the geometry editor 252.

Figure 21:
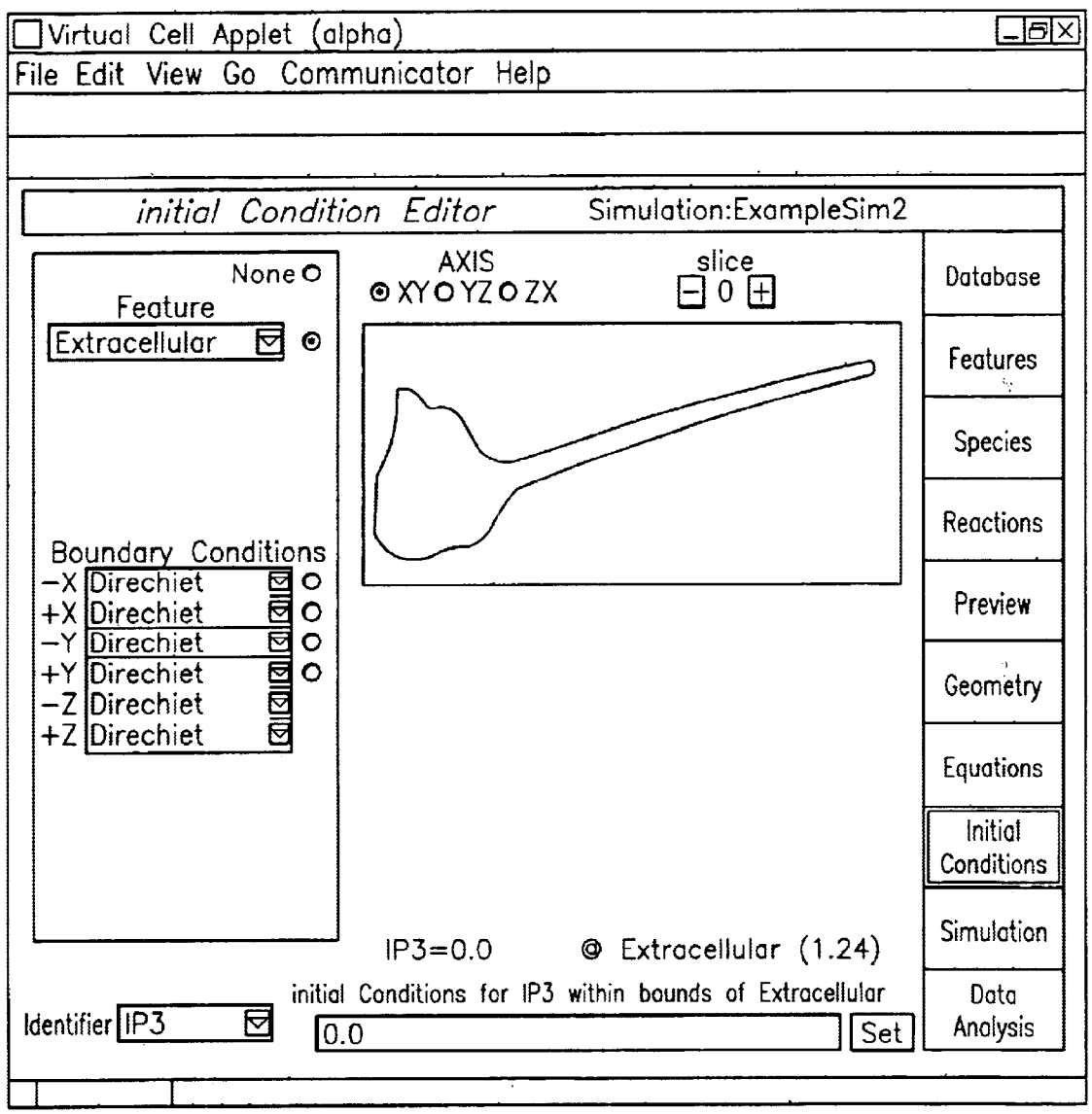

The spatial simulation module 250 includes an initial condition editor 254 which allows for the specification of initial conditions and boundary conditions for each of the species for each feature. The boundary conditions for each simulation border are specified independently for each feature, this gives maximum flexibility. For example, the concentrations may be specified at simulation boundaries in the extracellular space to indicate a sink. And a zero molecular flux may be specified at a simulation boundary belonging to cytosol to indicate symmetry of function with the missing portion of cytosol (the implied mirror image). FIG. 21 depicts an exemplary interface with the initial condition editor 254.

The spatial simulation module 250 includes a simulation controller 256 which permits the specification of the time step and end times of the currently defined spatial simulation. The simulation controller 256 services are then invoked, including automatic code generation and the initiation of a remote simulation job. The time step is automatically determined and will generally be constrained by the problem and the spatial discretization.

Figure 22:
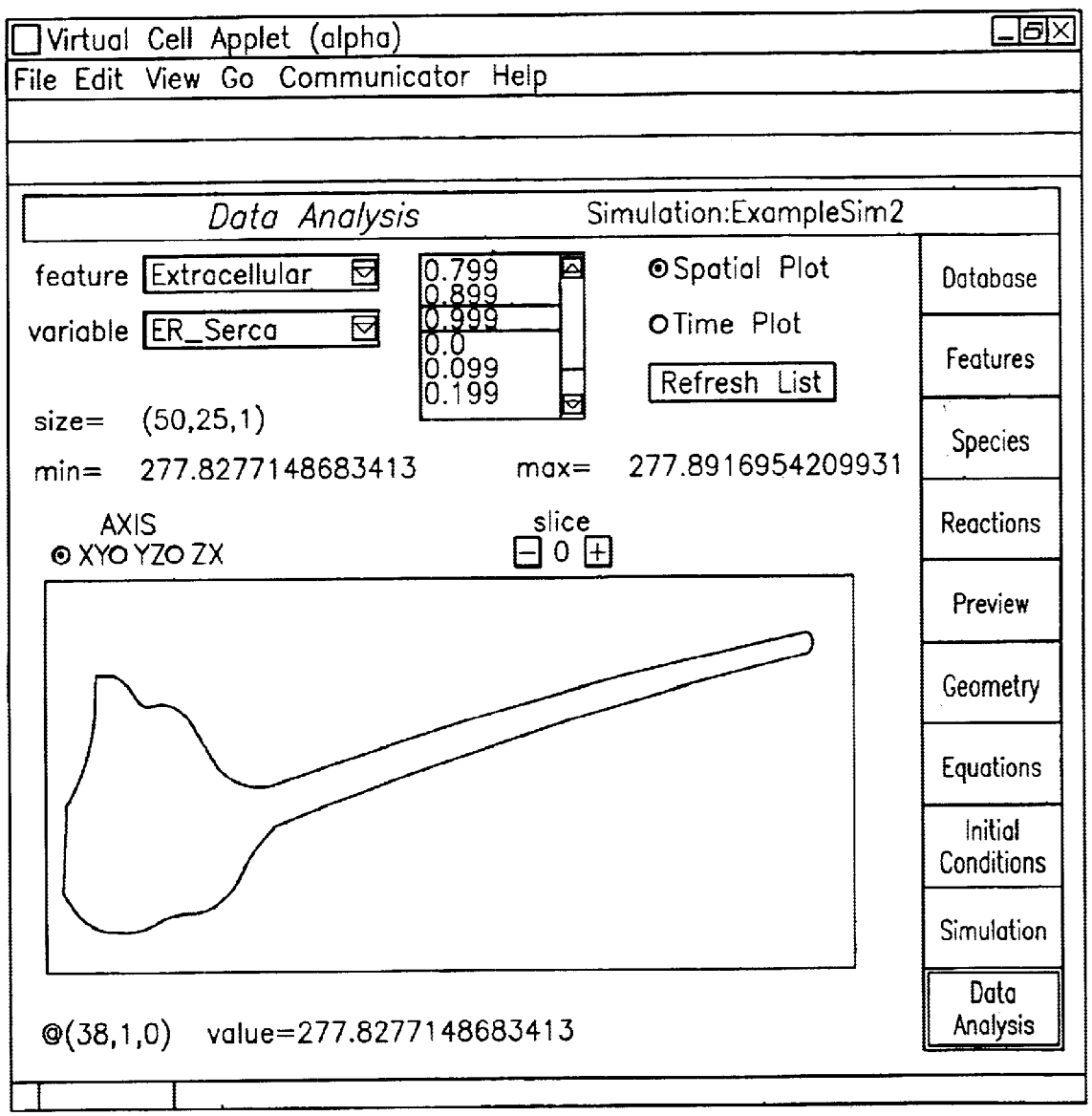
Figure 23:
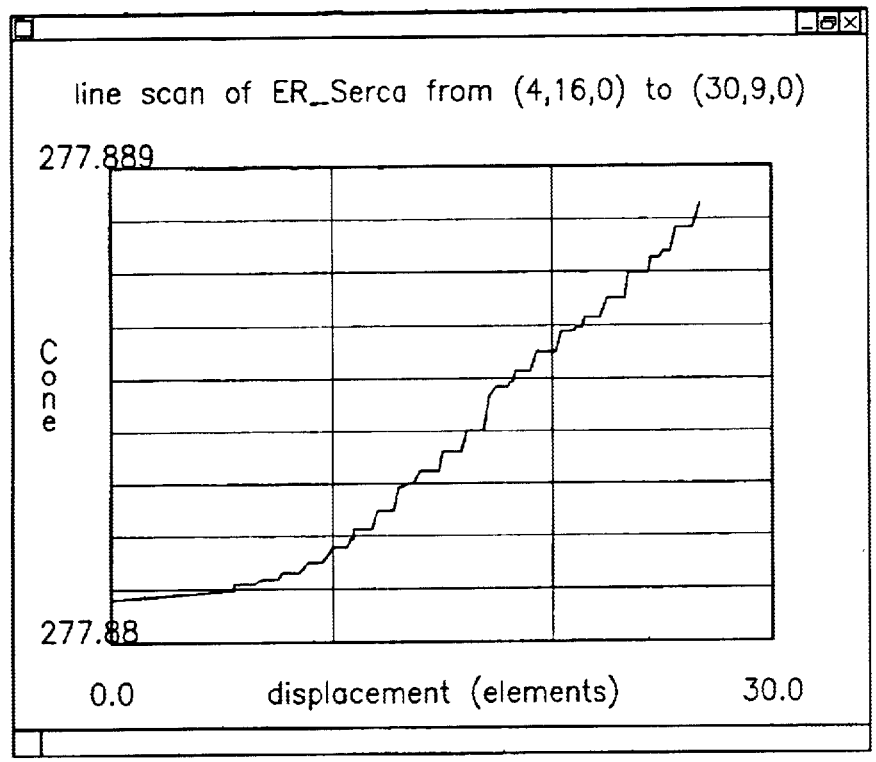
Figure 24:
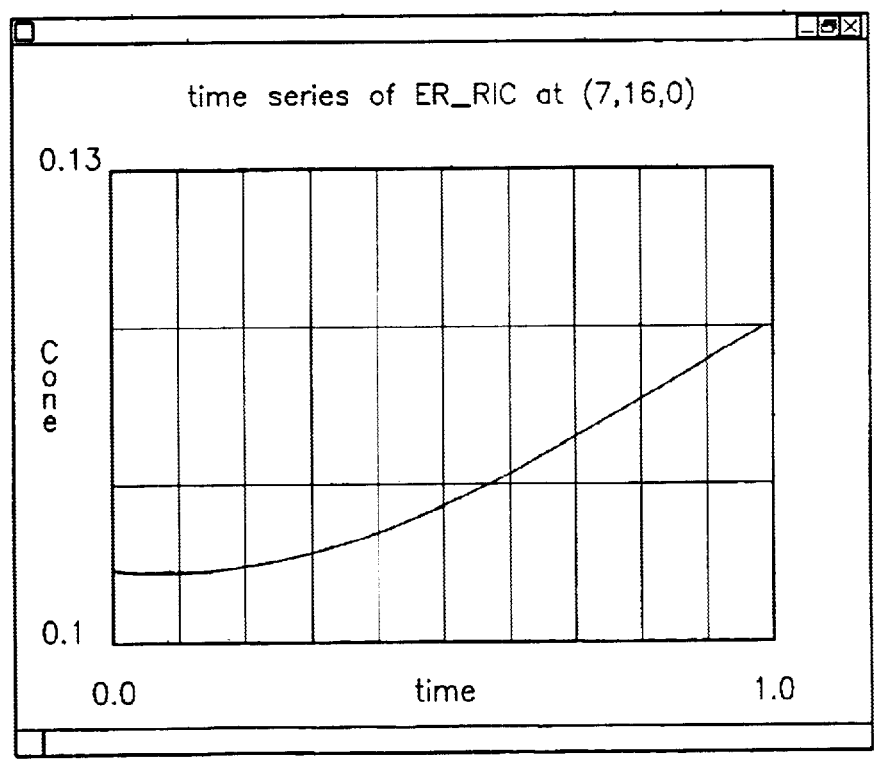

The spatial simulation module 250 includes a simulation data analyzer 258 which displays the results of the current spatial simulation. The species concentrations are displayed superimposed on the mesh. FIG. 22 depicts an exemplary interface with simulation data analyzer 258. The analysis capability available includes graphing the spatial distribution of a species as a line scan as shown in FIG. 23 and graphing a time series at a single point as shown in FIG. 24.

Figure 25:
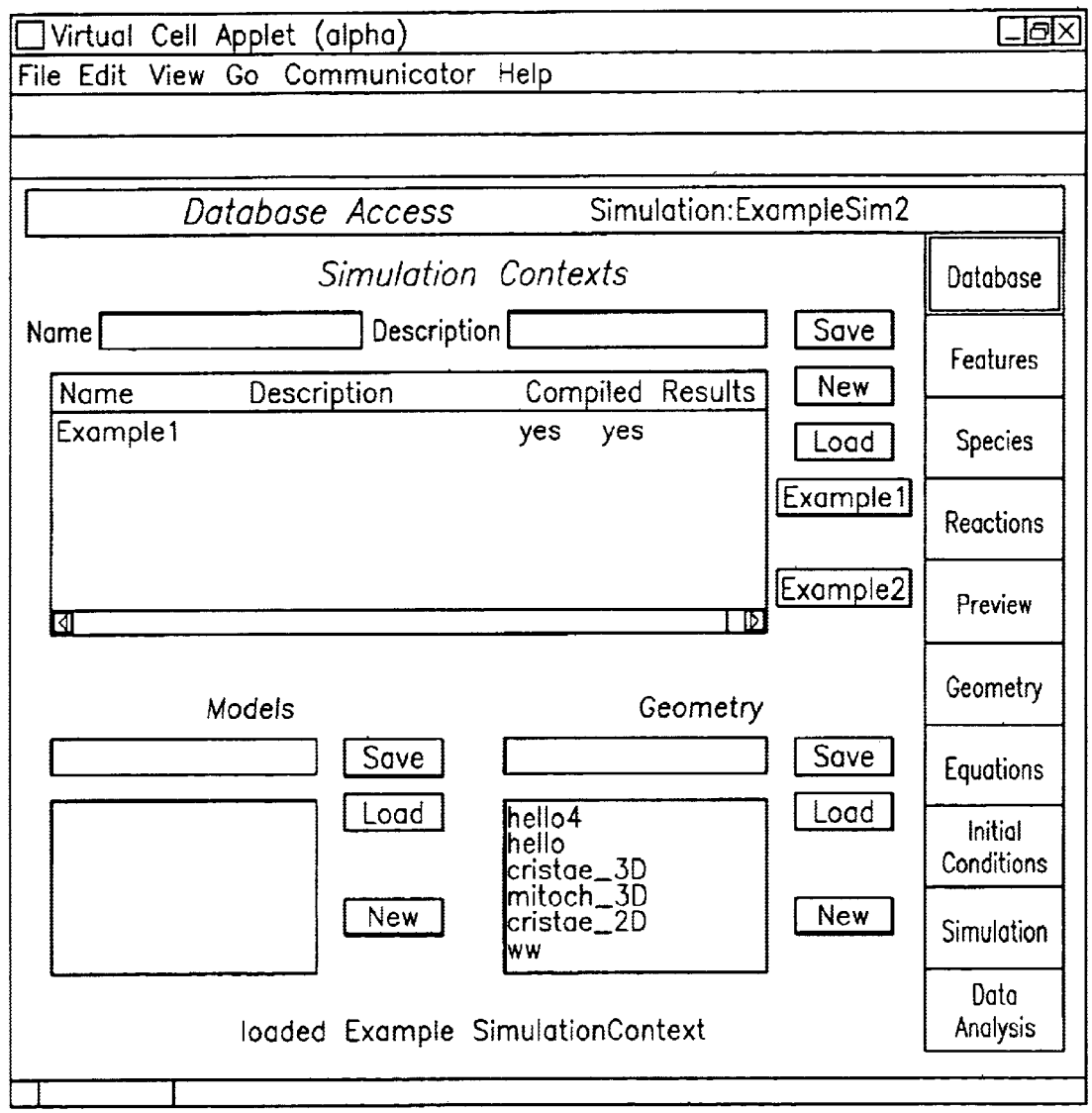

The storage module 240 includes a database access module 242 which presents a rudimentary model and simulation storage capability. The system allows whole physiological models, geometric models, and simulation contexts to be stored and retrieved. The simulation context is stored in a way that includes the physiological and geometric models such that it encapsulates all of the information to reproduce and describe a particular spatial simulation. FIG. 25 depicts an exemplary interface with the database access module 242.

The user interface may include a reaction interface that separates stoichiometry from kinetics. Common kinetic forms can be selected, or users can define their own. This allows for a structured context for reaction parameters. The specification of a simulation context may be augmented with experimental entities such as sources and sinks. Sources are externally controlled fluxes of chemical species (or electric current) applied at a point or distributed throughout a region of the simulation domain (e.g. micropipettes or current mode electrode). Sinks are externally controlled values of chemical species (or electric potential) applied at a point or throughout a region of the simulation domain. Currently, sources and sinks are defined only at simulation boundaries (Direchlet or Neumann boundary conditions).

Simulation output visualization and data analysis may include stochastic behavior of discrete macromolecules as well as electrical phenomena. Also, fundamental quantities of reaction models (such as pump fluxes, binding rates, and reaction rates) may be calculated from state variables and provided for visualization and analysis.

The present invention provides a framework that is a very general and flexible simulation tool that allows researchers to build on the experimental results and theoretical evaluations of others in an effort to better understand the interactions of cellular physiology. As related models are verified under various conditions and different cell lines, generalizations of related phenomena can be quantified in a structured way. In this way, individual researchers can use this as a tool to better understand their physiological application, while at the same time contributing to a shared knowledge base for the benefit of all. Although the invention has been described as a simulation method for cells, it is understood that the invention may be applied to the simulation of multiple cells (e.g. tissue). In addition, the simulation method is not limited to the simulation of biological events but may be applied to variety of real world events such as modeling electromechanical gas sensors with different geometry or interfaces to air. The chemical dynamics of any chemical process can be simulated using the method of the present invention. Accordingly, the invention has application beyond cellular simulations.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of simulating a biological material comprising:
   acquiring an n-dimensional geometric description of the biological material;
   linking at least one biological feature to a model defining physiological properties of said feature, said model defining a spatially independent model;
   associating said model with a region within said n-dimensional geometric description, thereby specifying a set of mathematical equations corresponding to processes in said region;
   creating a set of simulation elements defining a simulation volume from said n-dimensional description, each of said simulation elements corresponding to one of said regions; and
   simulating a physiological process for said biological material through said simulation elements, said simulation elements providing for the spatial discretization of said mathematical equations,
   wherein said model is selected from one of a species category of models, a feature category of models and a functional category of models.

2. The method of simulating a biological material of claim 1 wherein:
   said species category of models includes species models and membrane species models.

3. The method of simulating a biological material of claim 2 wherein:
   each of said species models represents a molecular species as a continuous concentration.

4. The method of simulating a biological material of claim 2 wherein:
   said species models represent molecular species as discrete particles.

5. The method of simulating a biological material of claim 2 wherein:
   said membrane species models represent a continuous surface density of a molecular species on a membrane.

6. The method of simulating a biological material of claim 2 wherein:
   said membrane species models represent a set of discrete membrane molecules on or in a membrane.

7. The method of simulating a biological material of claim 1 wherein:
   said feature category of models includes feature models and structural feature models representing topological organization of the biological material.

8. The method of simulating a biological material of claim 7 further comprising:
   mapping at least one of said feature category of models to said region.

9. The method of simulating a biological material of claim 8 wherein:
   said mapping includes spatial mapping wherein one of said feature category of models is mapped to one or more spatially defined regions in the biological material.

10. The method of simulating a biological material of claim 8 wherein:

said mapping includes distributed mapping wherein one of said feature category of models is mapped as a fraction of a region corresponding to its topological parent.

11. The method of simulating a biological material of claim 8 wherein:

said mapping includes compartmental mapping wherein one of said feature category of models is mapped to a region without spatial information.

12. The method of simulating a biological material of claim 7 wherein:

said feature category of models represent physiology within its topological constraints.

13. The method of simulating a biological material of claim 7 wherein:

said structural feature models represent boundaries within the biological material.

14. The method of simulating a biological material of claim 1 wherein:

said functional category of models represents physiological mechanisms in the biological material.

15. The method of simulating a biological material of claim 14 wherein:

said functional category of models includes reaction models representing chemical or biochemical reactions occurring in solution.

16. The method of simulating a biological material of claim 14 wherein:

said functional category of models includes membrane reaction models representing chemical or biochemical reactions occurring in a membrane.

17. The method of simulating a biological material of claim 14 wherein:

said functional category of models includes motion models representing diffusion.

18. The method of simulating a biological material of claim 14 wherein:

said functional category of models includes constrained motion models representing motion of an element constrained by a structure.

19. The method of simulating a biological material of claim 1 further comprising:

determining a sensitivity for said model, said sensitivity representing a degree of change in a model output in response to variation in a model parameter.

* * * * *